(12) United States Patent
Bonnette et al.

(10) Patent No.: US 7,951,161 B2
(45) Date of Patent: May 31, 2011

(54) ATHERECTOMY SYSTEM HAVING A VARIABLY EXPOSED CUTTER

(75) Inventors: Michael John Bonnette, Minneapolis, MN (US); Eric Joel Thor, Arden Hills, MN (US); Stephen Earl Weisel, Montrose, MN (US); David Brian Morris, Anoka, MN (US)

(73) Assignee: MEDRAD, Inc., Indianola, PA (US)

( * ) Notice: Subject to any disclaimer, the term of this patent is extended or adjusted under 35 U.S.C. 154(b) by 518 days.

(21) Appl. No.: 11/451,990

(22) Filed: Jun. 13, 2006

(65) Prior Publication Data

US 2007/0265647 A1   Nov. 15, 2007

Related U.S. Application Data

(60) Provisional application No. 60/798,961, filed on May 9, 2006.

(51) Int. Cl.
*A61B 17/22* (2006.01)
*A61B 17/32* (2006.01)

(52) U.S. Cl. ........ 606/159; 606/167; 606/168; 606/169; 606/170; 606/171; 606/180; 604/22

(58) Field of Classification Search ............ 604/22; 606/159, 166–171, 180
See application file for complete search history.

(56) References Cited

U.S. PATENT DOCUMENTS

| | | | |
|---|---|---|---|
| 1,902,418 A | 11/1931 | Pilgrim | |
| 3,358,677 A | 12/1967 | Sheldon | |
| 3,419,010 A | 12/1968 | Williamson | |
| 3,930,505 A | 1/1976 | Wallach | |
| 4,273,131 A * | 6/1981 | Olsen | 606/191 |
| 4,631,052 A | 12/1986 | Kensey | |
| 4,669,469 A | 6/1987 | Gifford, III et al. | |
| 4,690,672 A | 9/1987 | Veltrup | |
| 4,747,821 A | 5/1988 | Kensey et al. | |
| 4,790,813 A | 12/1988 | Kensey | |
| 4,842,579 A | 6/1989 | Shiber | |
| 4,883,459 A | 11/1989 | Calderon | |
| 4,898,574 A | 2/1990 | Uchiyama | |
| 4,913,695 A | 4/1990 | Plechinger et al. | |
| 4,913,698 A | 4/1990 | Ito et al. | |
| 4,950,238 A | 8/1990 | Sullivan | |
| 4,979,951 A | 12/1990 | Simpson | |
| 4,990,134 A | 2/1991 | Auth | |
| 5,037,431 A | 8/1991 | Summers et al. | |
| 5,135,482 A | 8/1992 | Neracher | |
| 5,135,483 A | 8/1992 | Wagner et al. | |
| 5,261,877 A | 11/1993 | Fine et al. | |
| 5,285,795 A | 2/1994 | Ryan et al. | |
| 5,314,407 A | 5/1994 | Auth et al. | |
| 5,345,937 A | 9/1994 | Middleman et al. | |
| 5,358,509 A | 10/1994 | Fine et al. | |
| 5,364,393 A | 11/1994 | Auth et al. | |
| 5,419,774 A * | 5/1995 | Willard et al. | 604/22 |
| 5,431,673 A | 7/1995 | Summers et al. | |
| 5,496,267 A * | 3/1996 | Drasler et al. | 604/22 |
| 5,507,760 A | 4/1996 | Wynne et al. | |
| 5,643,296 A | 7/1997 | Hundertmark et al. | |
| 5,674,232 A | 10/1997 | Halliburton | |
| 5,728,128 A | 3/1998 | Crickenberger et al. | |
| 5,779,721 A | 7/1998 | Nash | |
| 5,782,849 A * | 7/1998 | Miller | 606/159 |
| 5,788,667 A | 8/1998 | Stoller | |
| 5,879,361 A | 3/1999 | Nash | |
| 5,895,402 A | 4/1999 | Hundertmark et al. | |
| 5,928,218 A * | 7/1999 | Gelbfish | 604/540 |
| 5,938,672 A | 8/1999 | Nash | |
| 5,997,558 A | 12/1999 | Nash | |
| 6,027,514 A | 2/2000 | Stine et al. | |
| 6,080,170 A | 6/2000 | Nash et al. | |
| 6,299,622 B1 | 10/2001 | Snow et al. | |
| 6,447,525 B2 | 9/2002 | Follmer et al. | |
| 6,524,323 B1 | 2/2003 | Nash et al. | |
| 6,569,147 B1 | 5/2003 | Evans et al. | |
| 6,572,578 B1 | 6/2003 | Blanchard | |
| 6,623,496 B2 | 9/2003 | Snow et al. | |
| 6,638,233 B2 | 10/2003 | Corvi et al. | |
| 6,652,546 B1 | 11/2003 | Nash et al. | |
| 6,830,577 B2 | 12/2004 | Nash et al. | |
| 6,843,797 B2 | 1/2005 | Nash et al. | |
| 6,905,505 B2 | 6/2005 | Nash et al. | |
| 6,997,934 B2 | 2/2006 | Snow et al. | |
| 7,534,249 B2 | 5/2009 | Nash et al. | |
| 2002/0077642 A1 | 6/2002 | Patel et al. | |
| 2003/0125757 A1 | 7/2003 | Patel et al. | |
| 2004/0167554 A1 | 8/2004 | Simpson et al. | |
| 2005/0177068 A1 | 8/2005 | Simpson | |

FOREIGN PATENT DOCUMENTS

| | | |
|---|---|---|
| DE | 3421390 | 12/1985 |
| DE | 3715418 | 11/1987 |
| EP | 0232678 | 12/1986 |
| EP | 0329492 | 12/1989 |
| JP | 1085639 | 3/1989 |
| WO | WO8804157 | 6/1988 |
| WO | WO9005493 | 5/1990 |

* cited by examiner

*Primary Examiner* — Todd E Manahan
*Assistant Examiner* — Amy Lang
(74) *Attorney, Agent, or Firm* — David Schramm

(57) ABSTRACT

An atherectomy system having a variably exposed cutter wherein a distally located positionable tip closely associated with the cutter and a high pressure fluid jet emanator can be variably and angularly deployed about a hinge mechanism subsequent to entry into the vasculature. The fixed cutter slices or parts atheromatous material and/or thrombotic material from a blood vessel for interaction with high pressure jets to macerate, break up or otherwise reduce the materials for evacuation from the site.

36 Claims, 29 Drawing Sheets

| FIG. 13a | FIG. 13b | FIG. 13c |

FIG. 12

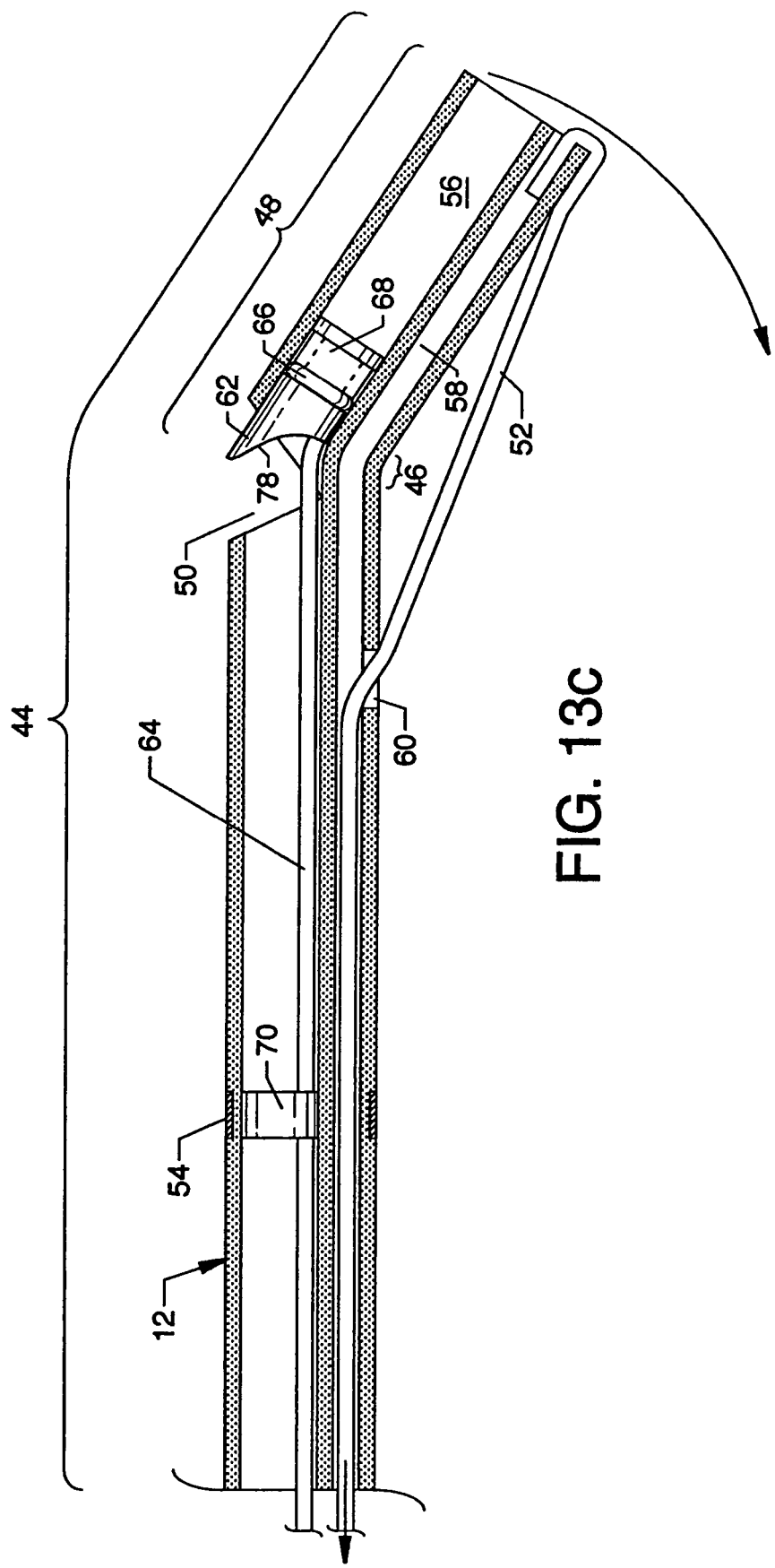

ATHERECTOMY SYSTEM HAVING A VARIABLY EXPOSED CUTTER

CROSS REFERENCES TO RELATED APPLICATIONS

This application claims benefit from the earlier filed U.S. Provisional Application No. 60/798,961 entitled "Atherectomy System Having a Variably Exposed Cutter", filed May 9, 2006, and is hereby incorporated into this application by reference as if fully set forth herein.

BACKGROUND OF THE INVENTION

1. Field of the Invention

The purpose of the present invention is to provide an improved atherectomy system where treatment of undesirable deposits in the vasculature ranging from soft clots to harder plaque is provided. The major problems faced by current atherectomy devices include vessel safety, embolization, and ease of use. Potentially, all of those issues are addressed by the design of and are incorporated into the operation of the present invention. Coagulated blood, fatty deposits, plaque, grumous or other built-up material generally referred to as thrombus is developed in-vivo in the body. As time goes on, this coagulated blood becomes more organized and tough. Thrombus that resides in the vessels even a few days can limit the impact of thrombectomy catheters, such as an AngioJet®, for complete removal. Thus, one potential application of the present invention is to remove organized clots that are resistant to traditional thrombectomy catheter treatment. Alternatively, arterial disease is a progression of atheromatous material, a soft fatty buildup within a blood vessel. The disease process is dependent upon a variety of factors including diet, exercise, patient genetic profile, diabetes, etc. The formation of atheromas in the heart is typically treated by coronary stenting procedures (Percutaneous Coronary Intervention ("PCI")). In the case of PCI, the stenotic portion of the vessel (a constricted section of the vessel due to thickening of the vessel wall with plaque deposits) is opened with a balloon and supported with a stent. In some cases, it may be desirable to remove a portion of the plaque rather than using a stent. For example, lesions in the vicinity of the ostium of a coronary artery may result in plaque shifting when stented, resulting in blockage of a different coronary artery. In those cases, it may be preferred to remove plaque, even if stenting is intended. In the case of peripheral arterial disease, there has not been a good track record of maintaining patent vessels in the leg arteries by using stents. Some of the difficulties with stenting the leg arteries are the severe flexing of the arteries. As one bends a knee, the arteries are bent as well. Structural supports, such as stents, are difficult to devise such that they provide the desired structural support and necessary flexibility. Recently there has been some interest in using atherectomy as an alternative to stenting of arterial lesions in the leg. The SilverHawk® device by Fox Hollow Technologies, Inc. of Delaware is an atherectomy device that is used primarily in the legs for arterial debulking. The present invention is similar to the Fox Hollow device in that both remove atheromatous material. However, the present invention offers a novel way of evacuating the debris as it is being removed that is not possible with the currently marketed Fox Hollow device.

2. Description of the Prior Art

Three notable marketed atherectomy devices include the Rotablator® (Boston Scientific Corporation), the SilverHawk® (Fox Hollow Technologies, Inc.), and the Simpson AtheroCath® Catheter (formerly with Guidant). In the case of the Rotablator®, a spinning burr is used to cut through tough material. The burr is designed to avoid damaging a healthy vessel and yet enable cutting of the plaque. Allegedly, the Rotablator® produces embolic debris while ablating the stenotic lesion. The tip of the Rotablator® becomes hot from the work performed so it is under a constant purge of saline. Thus, embolic debris is flushed into the vascular bed. Contrary to the statement above, there is some concern about the production of this embolic debris. Secondly, the Rotablator® system has been characterized as time intensive to set up. There are various connections required. Thus, ease of use is also a concern. The rotational aspect to the device means it is not a directional atherectomy device. Thus, if the plaque is positioned on one-half of the vessel, the device would still contact the healthy side of the vessel as it performed its atherectomy function.

The second device mentioned has made a large impact in the treatment of peripheral arterial disease. Since stenting has not proven ideally efficacious in the long term patency of the treated vessels, atherectomy has become popular. The SilverHawk® device uses a rotational cutter to skive away the plaque. It is a directional atherectomy device. Similar to the present invention, it has a bent tip to position the cutter against the atheroma. The device is reported to be acceptably easy to set up. The issues with the device involve vessel safety and embolization. Physician discussions of complications with peripheral interventions have involved the use of the SilverHawk® device followed by an observed perforation of the artery. Secondly, the device directs the skived material (it whittles out strips of the plaque versus sanding it away) toward the tip of the catheter. Once the tip is full of these skived strips, there have been reported instances of excess debris being sent distally (embolization). Therefore, the physician must constantly remove the device from the patient to unload the tip.

The AtheroCath® is similar to the Possis Medical, Inc. atherectomy device in U.S. Pat. No. 5,496,267. In the case of the AtheroCath®, a balloon directs an opening in the catheter against the lesion. A metal cutter is advanced and any material caught inside the opening is excised (like a biopsy). In the case of U.S. Pat. No. 5,496,267, the balloon directs the opening in an AngioJet® style atherectomy catheter against a lesion. Any material that is caught inside the opening is presumably macerated by the high velocity fluid jets. It is evident that the AngioJet® style device in U.S. Pat. No. 5,496,267 would at least afford a means of conducting atherectomy in a continuous process. The Simpson catheter would be difficult to operate in long stretches of diseased vessel. Furthermore, both devices suffer from not encouraging material to be removed. For example, imagine that the devices are 2 mm in diameter and that the stenosis is a hard circumferential stenosis with smooth surface and an ID of 3 mm. The balloon would push the devices against the hard material, but none would enter the cutting region since it is a hard smooth surface. Hence, no material would be removed.

Possis Medical, Inc. currently manufactures the AngioJet® system which is used in coronary arterial, peripheral arterial, and arterial venous access graft interventional procedures for the removal of thrombus. The AngioJet® system uses high velocity fluid jets to generate secondary flow patterns at the catheter tip for the dislodgement, maceration, and removal of thrombus. The AngioJet® system originated as an idea for removal of atheromatous material by directing high velocity fluid jets at the hard diseased tissue. However, the high velocity fluid jets will not distinguish between diseased tissue and the healthy vessel wall. Therefore, the catheter design evolved to direct the high velocity fluid jets internally inside the catheter. This design proved to be able to remove thrombus while leaving the vessel wall unharmed. Nevertheless, it was recognized years ago that these high velocity fluid jets could prove useful in removing atheromatous material as well. Possis Medical, Inc. patented an atherectomy device using these high velocity fluid jets, U.S. Pat. No. 5,496,267.

SUMMARY OF THE INVENTION

The general purpose of the present invention is to provide an atherectomy system having a variably exposed cutter.

According to one embodiment of the present invention, there is provided an atherectomy system having a variably exposed cutter whereby:

1. An atherectomy device based on the principles and use of both high velocity fluid jets and a positionally fixed cutter which are mounted at the distal end of a catheter tube having a positionable tip. The term cutter and fixed cutter referred to in the present invention are interchangeable to distinguish such as a cutter which does not rotate along the longitudinal axis thereof, such as referred to in prior art cutters. Moreover, the catheter tube includes a plastic covered nitinol section continuing as a plain uncoated nitinol section. The plain uncoated nitinol section includes a centrally located hinge mechanism delineating the start of a positionable tip. The catheter tube includes two lumens, a large lumen for passage of a guidewire, effluent waste, and a high pressure tube, and for locating a combined high pressure loop emanator and a saddle mount; and additionally includes a small lumen located parallel to the large lumen for passage of a deployment wire. A hub, a slide body, a slide tube, and a manifold are suitably connected to the proximal portion of the catheter tube which interactingly influence and positionally fix the geometry of the positionable tip. A suitable high pressure fluid source, high pressure fluid pump, an exhaust regulator, and a collection chamber are also incorporated.

2. The positionable tip at the distal end of the catheter tube can be deployably deformed about a hinge mechanism to form an angle with the immediate adjacent portion of the catheter tube just proximal to the hinge mechanism upon activation of a deployment wire extending internally nearly the length of the small lumen of the catheter tube and freely exiting the catheter tube in close proximity to the positionable tip. The angularly deployed positionable tip shape exposes the cutter and makes the cutter available to negotiate the atheromatous material. The degree to which the positionable tip is angled with respect to the immediate adjacent proximal portion of the catheter tube just proximal to the hinge mechanism affects the depth of cut.

3. The combination of the positionally fixed cutter with high velocity fluid jets removes the need for moving parts at the distal catheter tube positionable tip other than the deployment wire which is employed to angularly configure the positionable tip. This combination incorporating the use of a cutter with high velocity fluid jets provides better cutting. The cutter can generate focal mechanical forces at the cutting edge that are much greater than those generated by the high velocity fluid jets. However, the high velocity fluid jets are continually cleaning the cutter by macerating and evacuating debris. Otherwise, the cutter would plug up with debris and become ineffective. Thus, the complementary action of the cutter and high velocity fluid jets yields a mechanically simple yet efficacious cutting solution.

4. The combination of the high velocity fluid jets with the cutter also affords another advantage. The safety of the system can be modified in three ways. The more severe the depth of cut (the greater the angulation of the positionable tip), the more potentially injurious the catheter tube may be to the native vessel wall. Accordingly, the safety of the system can be affected by observing and reducing the deployment angle of the positionable tip. Similarly, the sharpness of the outward edge of the cutter will affect both the efficacy of the cutting and the safety of the catheter. A sharper external edge of the cutter has greater potential for injury to the vessel wall. Finally, the recirculating fluid can act as a lubricating layer to deflect the healthy pliable vessel, yet it would not deflect thickened hard plaque away from the cutter.

5. The catheter is directional in that the physician may wish to remove atheromatous material from one side and from an opposed side of the vessel. Hence, the catheter tube is torqueable. The incorporation of a braided metal polymer coated tube for the proximal end of the catheter ensures the device has appropriate rotational steerability to access the full inner circumference of the atheromatous material site.

6. The positionable tip of the catheter has a nitinol support structure functioning as a hinge mechanism. The mechanical properties of nitinol ensure that the positionable catheter tip can be bent or rotated about the hinge mechanism while maintaining appropriate mechanical support of the distal end of the catheter; i.e, the positionable tip. The positionable tip is formed of a tubular uncoated nitinol section with an appropriately shaped notch or gap placed in the center portion of the tubular uncoated nitinol section. The notch is essential and relevant in the formation and operation of the hinge mechanism. The deployment wire runs for the most part along the small lumen of the catheter tube and then exits the tubular uncoated nitinol section and extends externally to the most distal part of the positionable tip and attaches thereto. When actuated in a proximal direction, the deployment wire exerts force on the distal end section of the positionable tip to cause it to bend or deform in a reliable fashion about the hinge mechanism, thus exposing the cutter. Furthermore, if the deployment wire is relaxed, the superelastic properties of the nitinol return the positionable tip to its straight configuration. The notch and hinge mechanism operate to reveal the cutter. Hence, the notch and hinge mechanism allow useable revealing of the fixed cutter and also accomplish elastic recovery of the positionable tip. Alternatively, a PEBAX® catheter body can be a separate structure affixed to the end of the nitinol hinge.

The various embodiments of the atherectomy system having a variably exposed cutter have several significant aspects and features.

One significant aspect and feature of the present invention is a catheter tube having a large lumen and a small lumen.

Another significant aspect and feature of the present invention is the use of a variably exposed cutter to skive or slice material ranging from atheromatous material to organized thrombotic deposits from the vascular system.

Yet another significant aspect and feature of the present invention is the use of high velocity fluid jets emanating from a high pressure loop emanator to break up, erode and be instrumental in the removal of skived material ranging from atheromatous material to organized thrombotic deposits from the vascular system.

Yet another significant aspect and feature of the present invention is the use of high velocity fluid jets emanating from a high pressure loop emanator to directly break up, erode and be instrumental in the removal of material ranging from atheromatous material to organized thrombotic deposits adhering to the interior of the vascular system.

Still another significant aspect and feature of the present invention is the concurrent use of a cutter and high velocity fluid jets to remove material ranging from atheromatous material to organized thrombotic deposits adhering to the interior of the vascular system.

Still another significant aspect and feature of the present invention is the use of high velocity fluid jets to urge atheromatous material, organized thrombotic material and the like proximally along the large lumen of the catheter tube for disposal.

Another significant aspect and feature of the present invention is the use of a hinge mechanism having positional memory.

Another significant aspect and feature of the present invention is the use of either a closely coupled or elongated hinge mechanism located in a distally located uncoated nitinol section of a catheter tube which is incorporated into use as a living hinge in close association with one or more cutters and with a high pressure loop emanator.

Another significant aspect and feature of the present invention is the availability of the cutter and high velocity fluid jets for use when the positionable tip is angularly deployed.

Still another significant aspect and feature of the present invention is an atherectomy system having a cutter with controllable angular orientation.

Yet another significant aspect and feature of the present invention is the use of a slide body engaged within a slide tube to adjustably and fixingly influence the angular displacement of a positionable tip about a hinge mechanism.

Additionally, in certain embodiments of the present invention a significant aspect and feature is the use of a deployment wire extending along the entire length of a small lumen in the catheter tube with the distal end of the deployment wire being secured within the distal portion of the small lumen of the catheter tube, or the deployment wire can extend the greater interior length of a small lumen in the catheter tube to exit from an orifice to extend distally along the exterior of the catheter tube to connect to the distal end of an uncoated nitinol section of the catheter tube known as the positionable tip, each method of which is incorporated for deploying and variably controlling the angular position of the positionable tip.

Additionally, in certain embodiments a significant aspect and feature is the use of a stabilized substitute elongated and flexible cutter extending distally and proximally a substantial distance beyond the region of a hinge mechanism.

Additionally, in a first, a second, and a third alternative embodiment a significant aspect and feature is the use of formed and flexible angled deployment actuators, preferably of nitinol, generally in a shaped rod form in lieu of a deployment wire which extends along the small lumen of the catheter tube to cause angulation or bending of the positionable tip about the hinge mechanism.

Additionally, in the first alternative embodiment a significant aspect and feature is the use of a cutter having a proximally facing cutting edge attached to a high pressure loop emanator.

Additionally, in the second alternative embodiment a significant aspect and feature is the use of a cutter having a distally facing cutting edge spaced across a hinge mechanism in opposition to a high pressure loop emanator.

Additionally, in the third alternative embodiment a significant aspect and feature is the use of facing opposed cutters spaced across a hinge mechanism.

Having thus briefly described embodiments of the present invention and having mentioned some significant aspects and features of the present invention, it is the principal object of the present invention to provide an atherectomy system having a variably exposed cutter.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 7 shows the respective orientation and alignment of FIGS. 8a and 8b;

FIG. 10 shows the respective orientation and alignment of FIGS. 11a and 11b;

FIG. 12 shows the respective orientation and alignment of FIGS. 13a, 13b and 13c;

FIGS. 13a, 13b and 13c together are an assembled foreshortened view in cross section of the components of FIGS. 8a and 8b and FIG. 4;

DETAILED DESCRIPTION OF THE PREFERRED EMBODIMENTS

Figure 1:
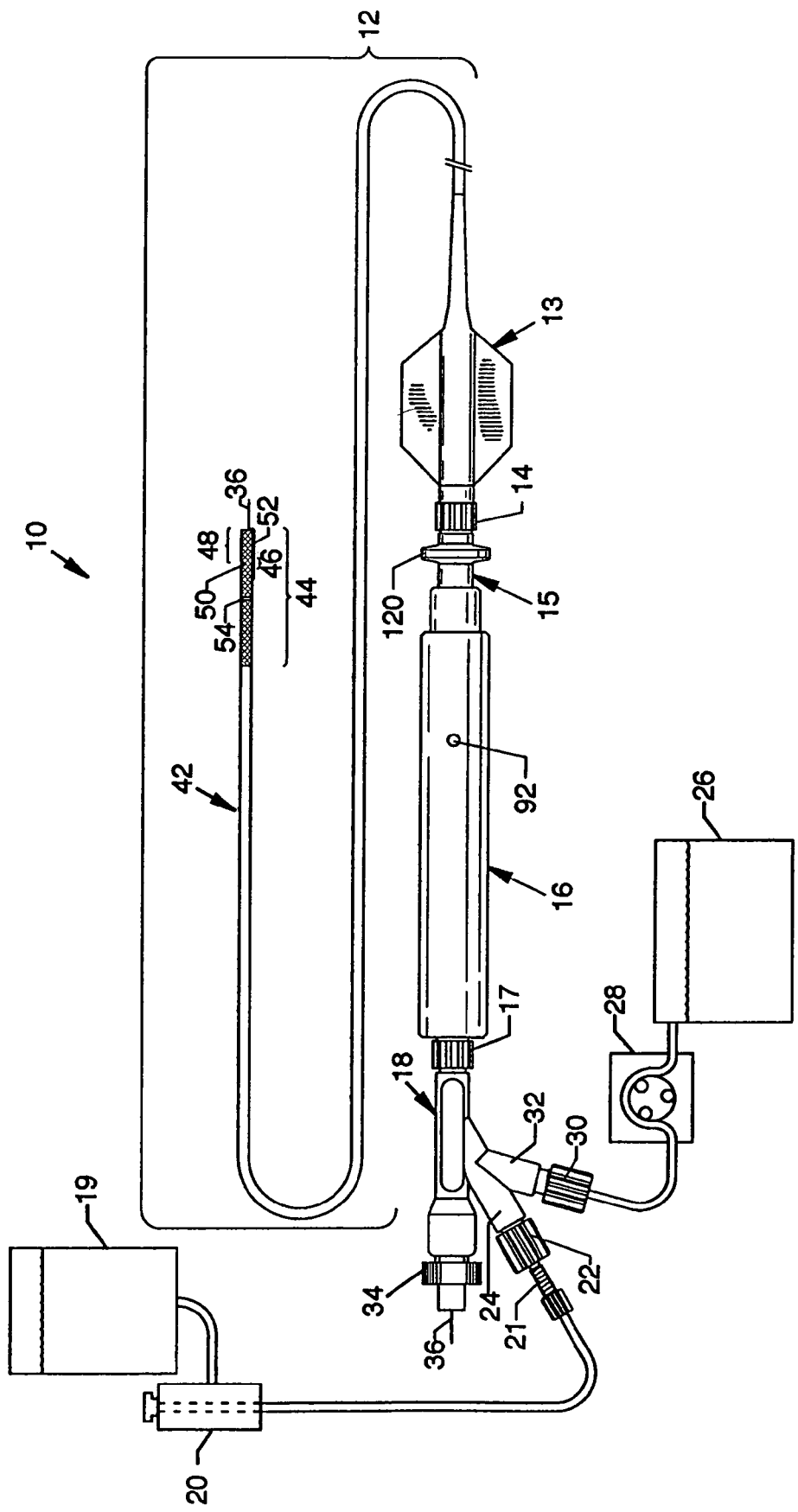
FIG. 1 is a plan view of an atherectomy system having a variably exposed cutter, the present invention.

FIG. 1 is a plan view of an atherectomy system having a variably exposed cutter 10, the present invention. A catheter tube 12 is connected to other aligned and connected components of the system including a hub 13, a connector fitting 14, a slide body 15, a slide tube 16, a connector fitting 17, and a manifold 18. A high pressure fluid source 19 in association with a high pressure fluid pump 20 is suitably connected to a high pressure branch 24 of the manifold 18 by flexible or other tubing and connector fittings 21 and 22. Also suitably connected to the manifold 18 by flexible or other tubing and a connector fitting 30 via an exhaust branch 32 of the manifold 18 is a collection chamber 26 in association with an exhaust regulator 28. A hemostatic nut 34 engages the proximal end of the manifold 18 for suitable sealed interaction with a guidewire 36. The catheter tube 12 has multiple lumens and is formed of a plastic coated nitinol section 42 and a nitinol section 44 without a plastic coating continuous therewith extending distally. The distal portion of the hub 13 is utilized for connection to the proximal end of the catheter tube 12, i.e., the plastic coated nitinol section 42. The uncoated nitinol section 44, the structure and features of which are part of the catheter tube 12, includes a hinge mechanism 46 and a portion of the uncoated nitinol section 44 distal to the hinge mechanism 46 referred to as the positionable tip 48. Also shown at the distal portion of the uncoated nitinol section 44 is a notch 50 interrupting the uncoated nitinol section 44 of the catheter tube 12 in close association with the hinge mechanism 46. A distal portion of a deployment wire 52 exits the catheter tube 12 through the uncoated nitinol section 44 and extends distally to connect to the end of the positionable tip 48. The proximal end of the deployment wire 52 exits a passage at the proximal end of the slide tube 16 and is positionally anchored or affixed therein or thereto, as later described in detail. A radiopaque ring 54 is also shown surrounding the uncoated nitinol section 44 of the catheter tube 12 proximal to the notch 50.

Figure 2:
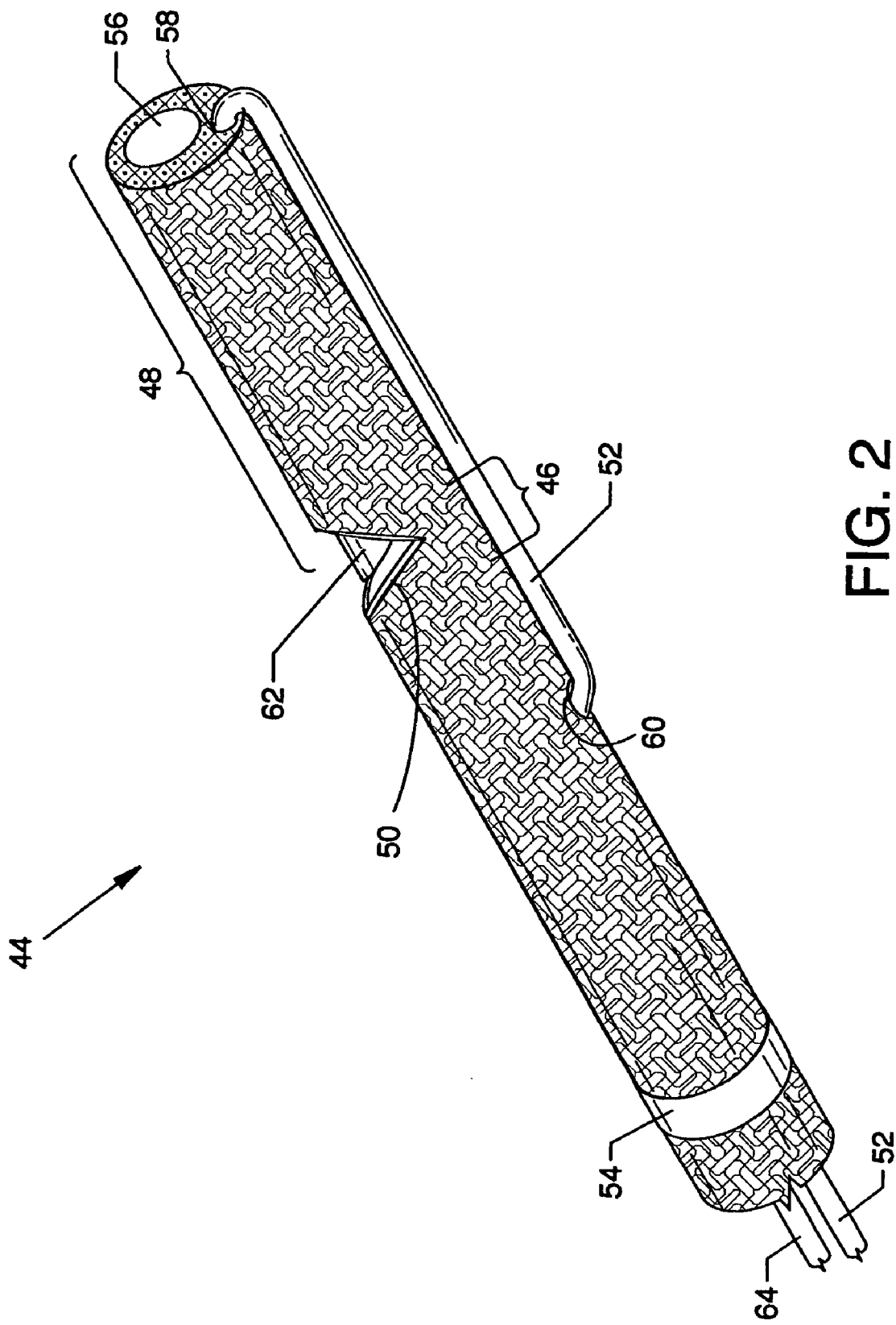
FIG. 2 is an isometric view of an uncoated nitinol section of a catheter tube.

FIG. 2 is an isometric view of the distally located uncoated nitinol section 44 of the catheter tube 12. Shown in particular is the positionable tip 48 which is the portion of the uncoated nitinol section 44 starting at and distal to the notch 50. The hinge mechanism 46 is shown including the area of the uncoated nitinol section 44 lying directly beneath the notch 50. The hinge mechanism 46 interfaces between the positionable tip 48 and the region of the uncoated nitinol section 44 immediately proximal to the notch 50, whereby the positionable tip 48 can be angularly positioned relative to the near portion of the uncoated nitinol section 44 just proximal to the hinge mechanism 46. Also shown are the distal portions of a large lumen 56 and a small lumen 58 extending along the length of the catheter tube 12, the large lumen 56 being interrupted by the notch 50. The deployment wire 52 is shown exiting through an orifice 60 of the small lumen 58 located at a location proximal to the notch 50 of the uncoated nitinol section 44. The deployment wire 52 extends from the orifice 60 in a distal direction along the exterior of the positionable tip 48 to connectingly terminate in the distal end of the small lumen 58. A portion of a cutter 62, later described in detail, is shown in the notch 50. Alternatively, the uncoated nitinol section 44 could be composed of another material, such as, but not limited to, PEBAX®, attached generally to the distal end of the plastic coated nitinol section 42.

Figure 3:
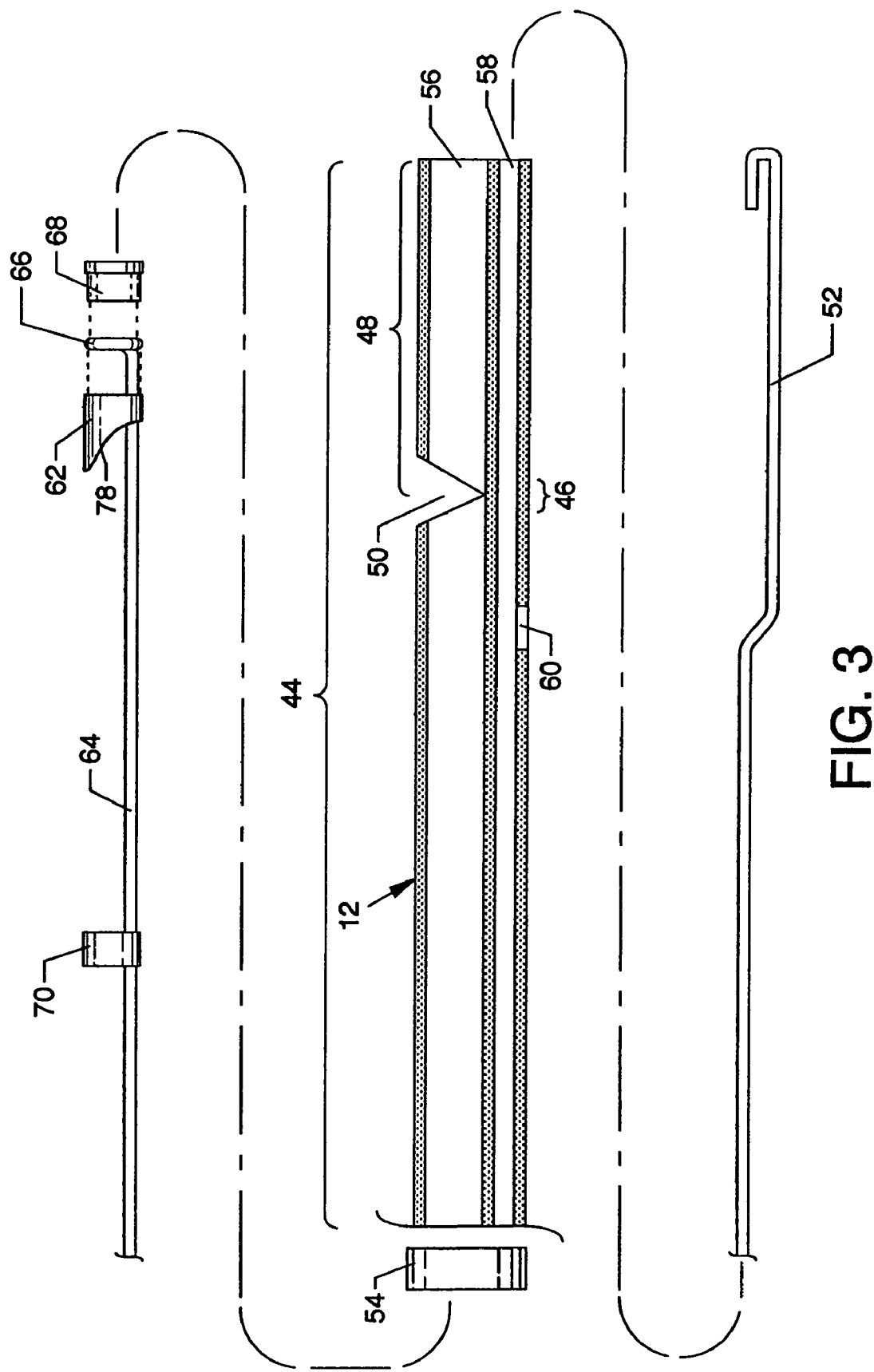
FIG. 3 is an exploded view showing the uncoated nitinol section and closely associated components at the distal end of the catheter tube, the uncoated nitinol section being shown in cross section.
Figure 4:
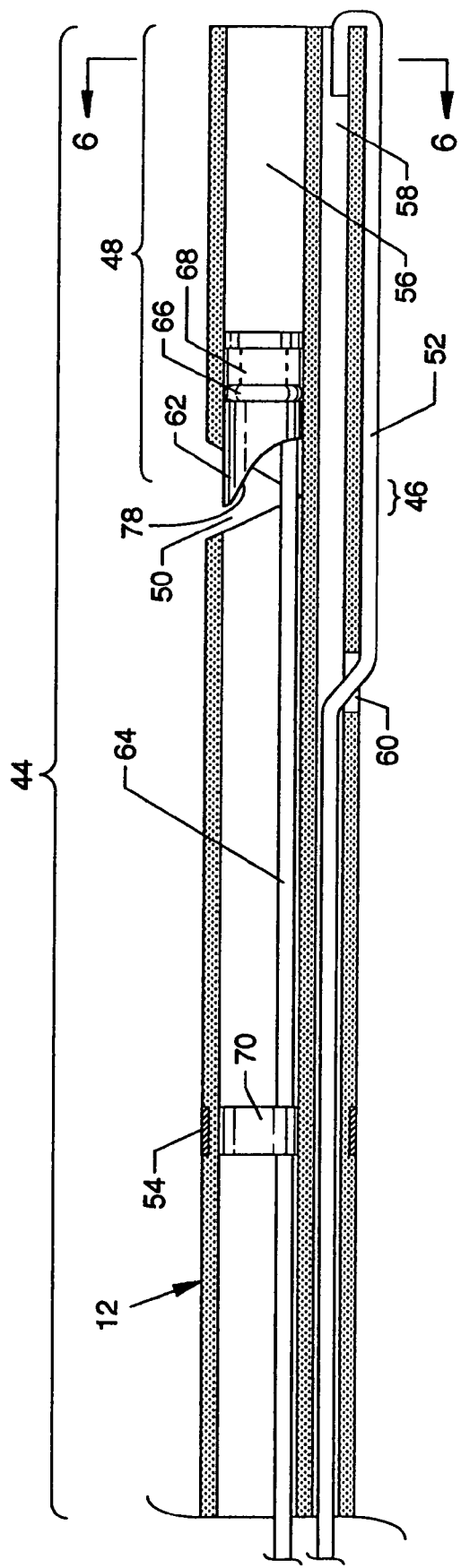
FIG. 4 is a view of the components shown in FIG. 3 assembled.

FIG. 3 is an exploded view showing the uncoated nitinol section 44 and closely associated components at the distal end of the catheter tube 12, the uncoated nitinol section 44 being shown in cross section; and FIG. 4 is a view of the components shown in FIG. 3 assembled. Especially shown is a greater portion of the uncoated nitinol section 44 and components which align within and thereto. A high pressure tube 64 for delivery of high pressure saline extends along the greater length of the large lumen 56 and extends from the connector 21 at the manifold 18, through the manifold 18, through the large lumen 56 traversing the notch 50 and extending distally beyond the notch 50 a short distance to the positionable tip 48 at the distal region of the uncoated nitinol section 44 to terminate as a high pressure loop emanator 66. The cutter 62 and a saddle mount 68, each of metal or other suitable material, secure such as by weldments or other suitable methods to opposing sides of the high pressure loop emanator 66, as further described with reference to FIG. 5. The cutter 62 is secured to the proximal facing surface of the high pressure loop emanator 66 and the saddle mount 68 is secured to the distal facing surface of the high pressure loop emanator 66. The cutter 62, the high pressure loop emanator 66, and the saddle mount 68 align as a unit in the large lumen 56 of the positionable tip 48. A proximal facing cutting edge 78 of the cutter 62 is shown extending partly into the notch 50. The cutter 62, the high pressure loop emanator 66, and the saddle mount 68 as a unit are in close alignment to the portion of the large lumen 56 located in the positionable tip 48, but do not frictionally engage the large lumen 56 so that the bending or flexing of the positionable tip 48 about the hinge mechanism 46 is unencumbered and not impeded. The high pressure tube 64 is suitably secured, such as by a weldment or other suitable attachment method, to the interior of a support ring 70 for use in close frictional association with the radiopaque ring 54, whereby the high pressure tube 64 is secured to the uncoated nitinol section 44 of the catheter tube 12.

Figure 5:
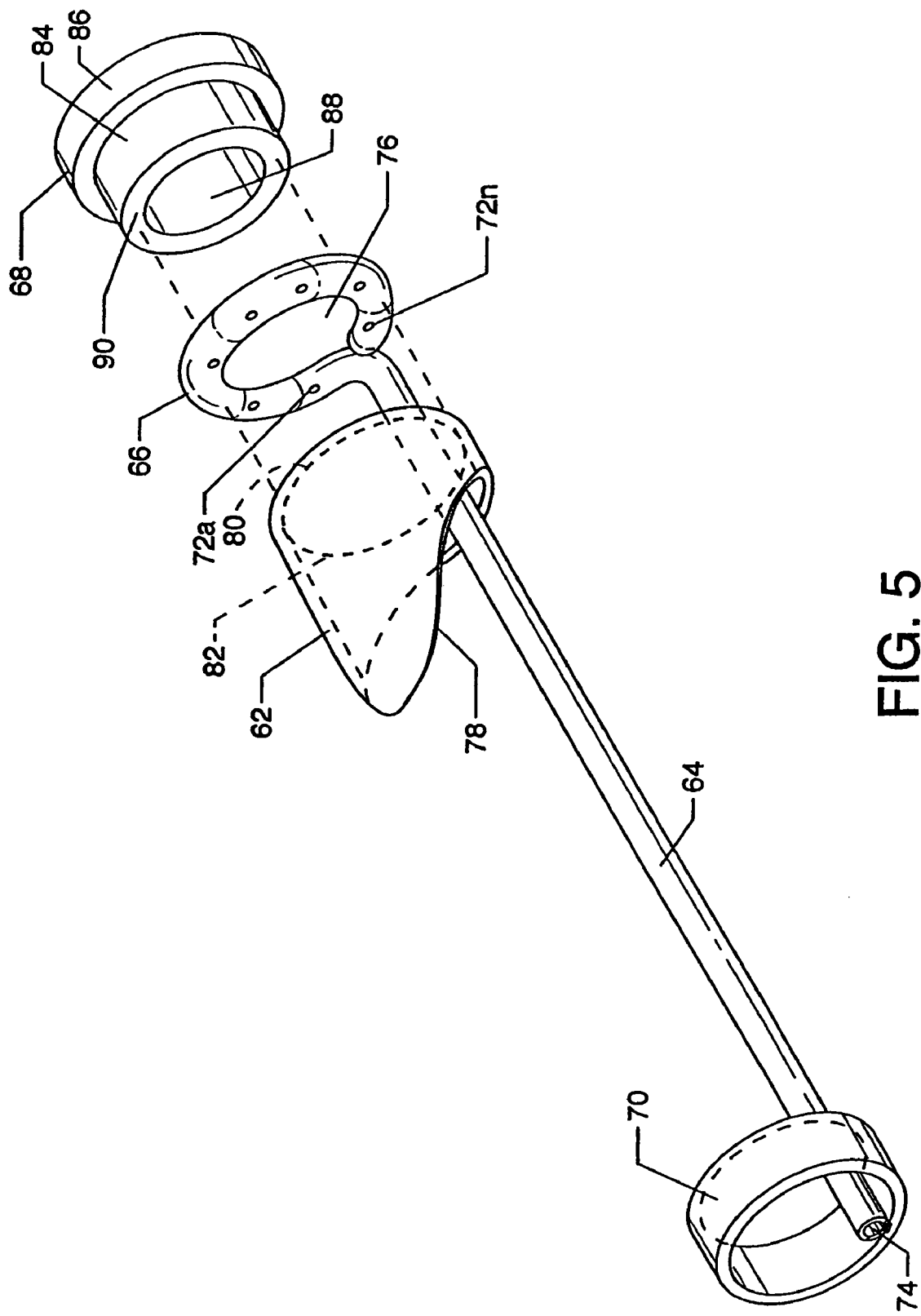
FIG. 5 is an exploded isometric view showing components which reside in or which are directly or closely associated with the positionable tip.

FIG. 5 is an exploded isometric view showing components which reside in or which are directly or closely associated with the positionable tip 48. The high pressure loop emanator 66 includes a plurality of proximally facing jet orifices 72a-72n on the proximal face thereof, each in communication with a lumen 74 of the high pressure tube 64. A passage 76 is formed by the high pressure loop emanator 66. The cutter 62 is of truncated tubular form including the sharp cutting edge 78 of suitable geometric configuration opposing an annular surface 80. A passage 82 connects the cutting edge 78 and the annular surface 80. The annular surface 80 secures appropriately, such as by a weldment or other suitable method, to the proximal facing portion of the high pressure loop emanator 66 in a manner whereby the plurality of jet orifices 72a-72n are not restricted. The saddle mount 68 is of multiple radius tubular construction including a minor radius portion 84 and an adjoining major radius portion 86. A passage 88 extends through the saddle mount 68. An annular surface 90 is formed at the proximal end of the saddle mount 68. The annular surface 90 appropriately secures, such as by a weldment or other suitable method, to the distal facing portion of the high pressure loop emanator 66.

Figure 6:
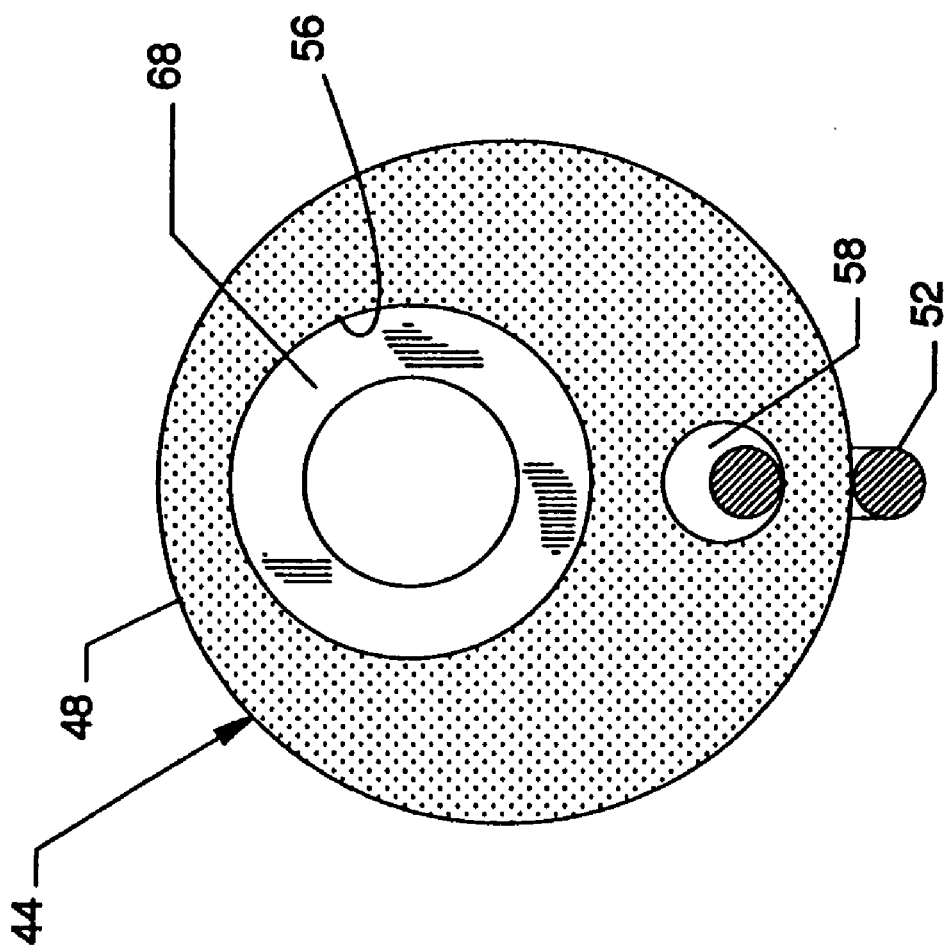
FIG. 6 is a cross section view along line 6-6 of FIG. 4.

FIG. 6 is a cross section view along line 6-6 of FIG. 4.

Figure 8A:
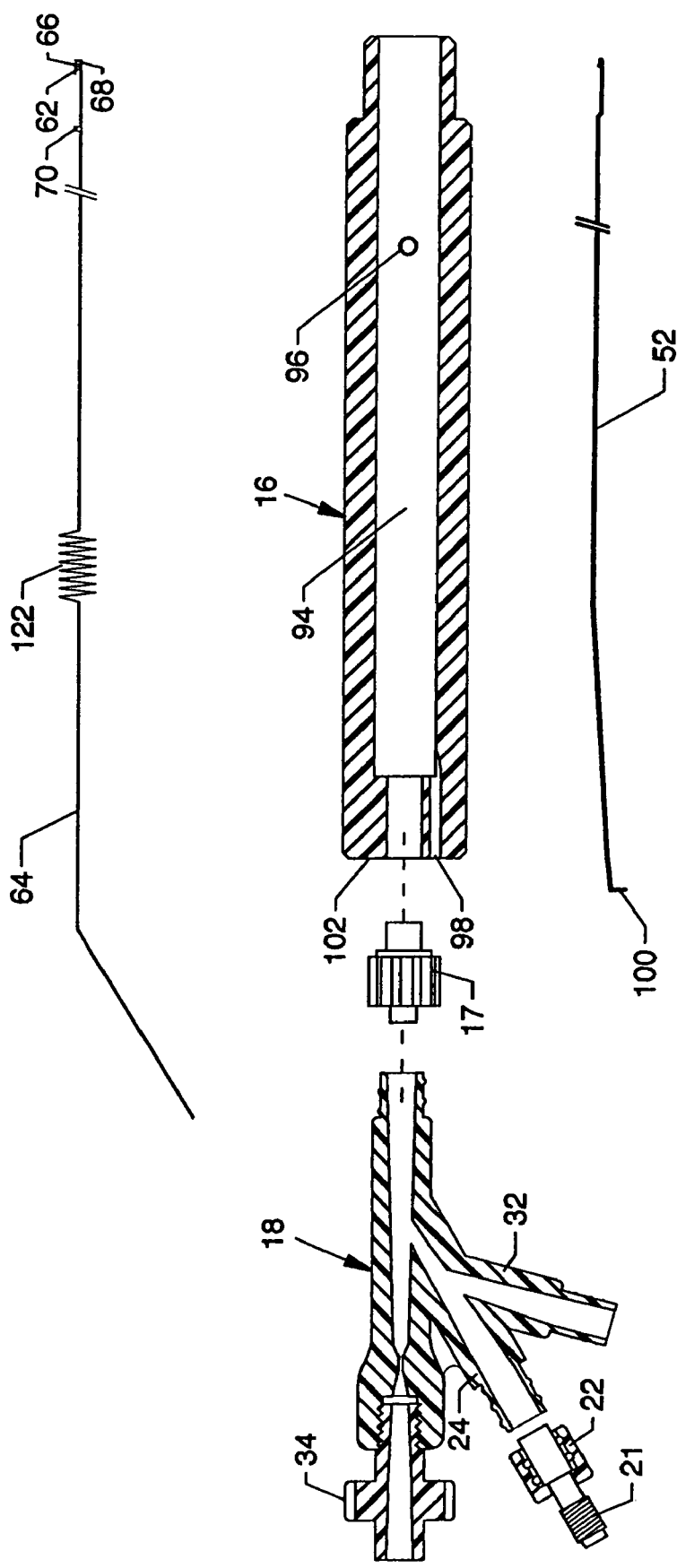
FIGS. 8a and 8b together are an exploded partial cross section view of components located proximal to the catheter tube and other components attached to and/or closely associated therewith.
Figure 8B:
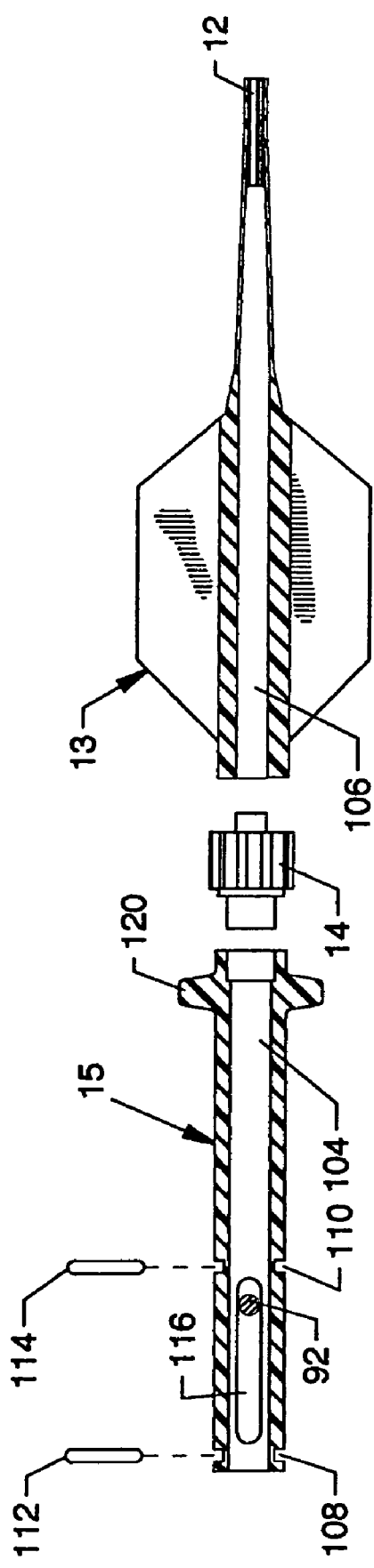

FIG. 7 shows the respective orientation and alignment of FIGS. 8a and 8b.

FIGS. 8a and 8b together are an exploded partial cross section view of components located proximal to the catheter tube 12, including the hub 13, the connector fitting 14, the slide body 15, the slide tube 16, the connector fitting 17, the manifold 18, the deployment wire 52, and the high pressure tube 64, and other components attached to and/or closely associated therewith.

Figure 9:
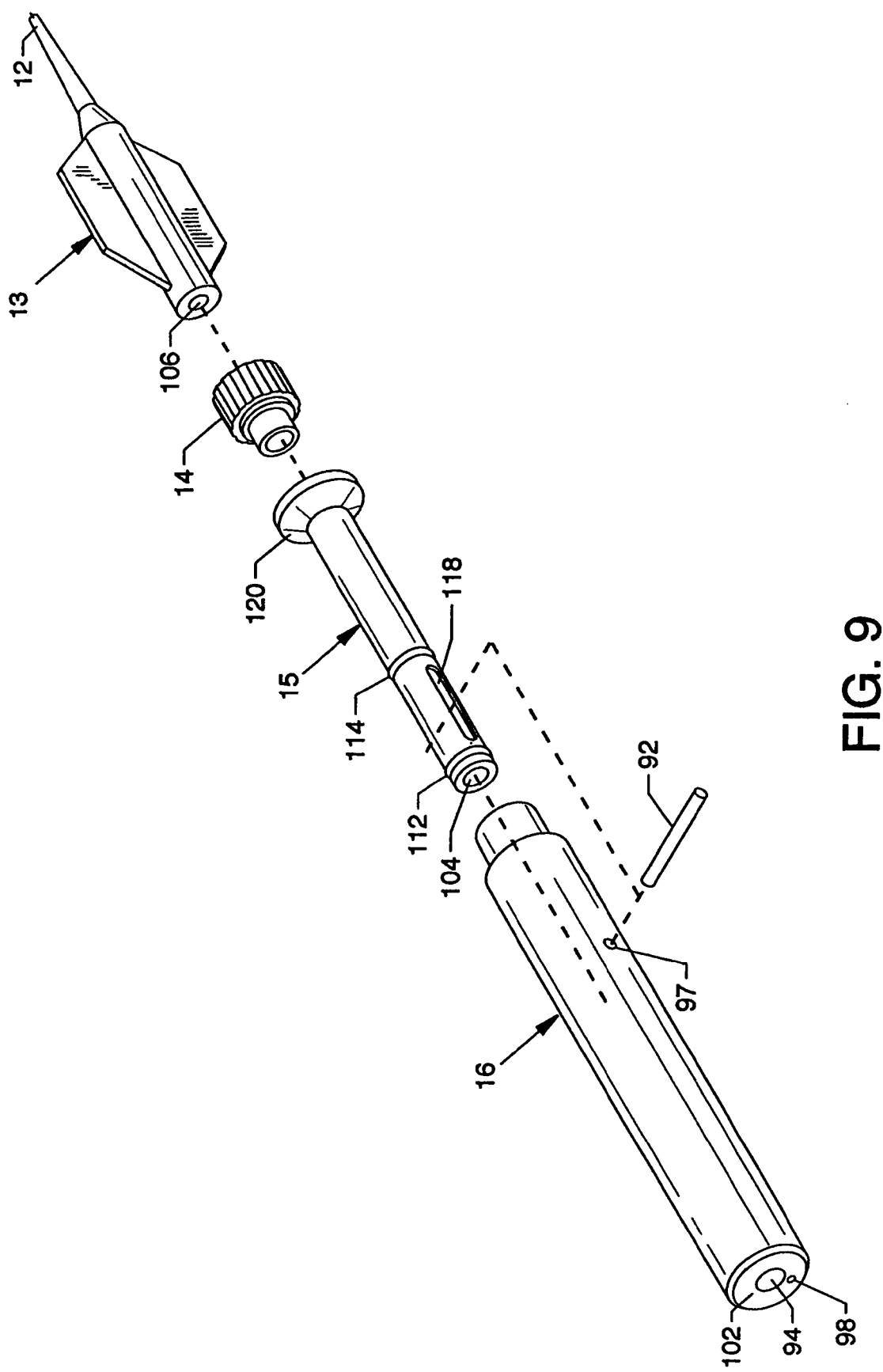
FIG. 9 is an exploded isometric view of the hub, the connector fitting, the slide body, the slide tube and a guide pin.

FIG. 9 is an exploded isometric view of the hub 13, the connector fitting 14, the slide body 15, the slide tube 16, and a guide pin 92.

Figure 11A:
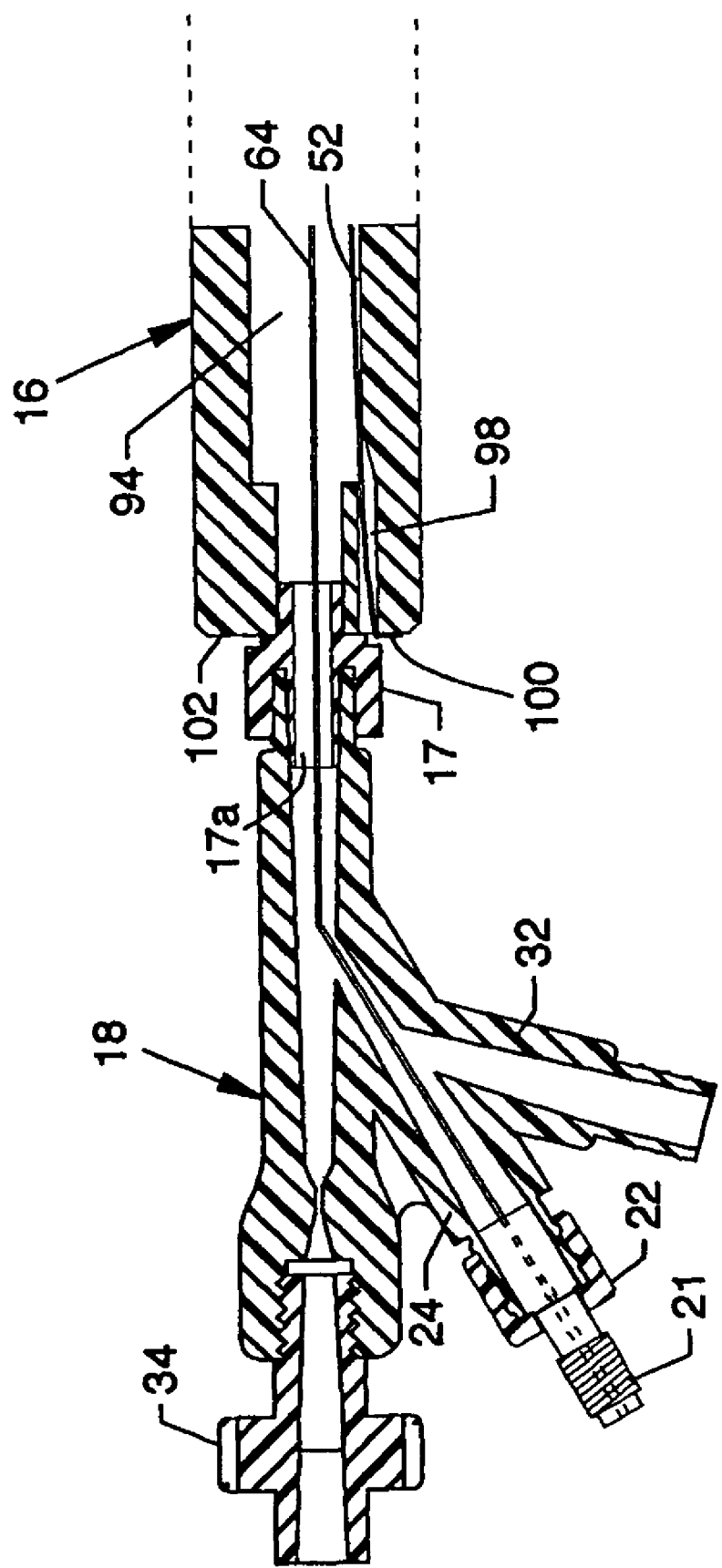
FIGS. 11a and 11b together are an assembled cross section view of the components of FIGS. 8a and 8b.
Figure 11B:
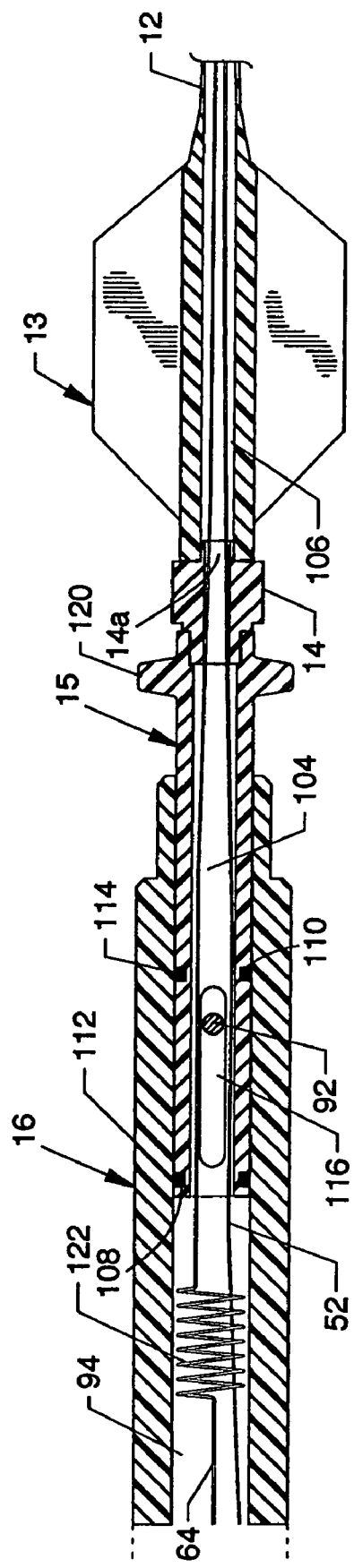

FIG. 10 shows the respective orientation and alignment of FIGS. 11a and 11b.

FIGS. 11a and 11b together are an assembled cross section view of the components of FIGS. 8a and 8b, including the hub 13, the connector fitting 14, the slide body 15, the slide tube 16, the connector fitting 17, the manifold 18, the deployment wire 52, and the high pressure tube 64, as well as other components attached to and/or closely associated therewith. Shown in particular is the slide body 15 in slidable frictional engagement with the slide tube 16, and the proximal portions of the deployment wire 52 and the high pressure tube 64 located therein, which are routed through the bore 17a of the connector fitting 17, the bore 94 of the slide tube 16, the bore 104 of the slide body 15, the bore 14a of the connector fitting 14, and the lumen 106 of the hub 13, and thence further routed along and through the large lumen 56 and the small lumen 58, respectively, of the catheter tube 12, as previously described. In this illustration, the nondeployed mode configuration relates to a nonangulated positionable tip 48, such as shown in FIG. 4, where the relationship of the slide tube 16 to the catheter tube 12 and connected slide body 15 is such that the slide tube 16 engages a maximum portion of the slide body 15 as shown.

With reference to FIGS. 4, 7, 8a, 8b, 9, 10, 11a and 11b, the instant invention is further described. Angular adjustability and retaining of the angulated position of the previously described positionable tip 48 about the hinge mechanism 46 is made possible and facilitated by the structure and the longitudinal relationship of the slide body 15 to the slide tube 16. The slide body 15 slidingly and frictionally engages the interior of the slide tube 16 by the use of interceding O-rings and can be manually adjusted by overcoming the frictional engagement thereof to influence the position of the slide body 15 to the slide tube 16. Such a positional association influences the relationship of the deployment wire 52 to the catheter tube 12 to position the positionable tip 48 about the hinge mechanism 46, as required.

The geometrically configured slide tube 16, preferably of nylon, is generally of a tubular shape including a bore 94 having multiple internal radii. The proximally located small radius portion of the bore 94 accommodates one end of the connector fitting 17 suitably secured therein, such connector fitting 17 having a longitudinal passage 17a for communication between the manifold 18 and the proximal small radius portion of the bore 94, as well as the adjoining and longer large radius portion of the bore 94. Opposed holes 96 and 97 extend through the wall of the slide tube 16 and are aligned perpendicular to the longitudinal centerline of the bore 94 for accommodation of opposing ends of the guide pin 92. An anchoring passage 98 extends from the proximal annular surface 102 of the slide tube 16 to communicate with the large radius portion of the bore 94 to allow passage of a proximal end 100 of the deployment wire 52 which positionally anchors or affixes therein or thereto. The proximal end 100 of the deployment wire 52 generally is angled from the major portion of the deployment wire 52 and can be geometrically configured to be closely juxtaposing the proximal annular surface 102 (FIG. 11a) in order to secure the proximal end of the deployment wire 52 in close association with the anchoring passage 98. The distal end of the deployment wire 52 is anchored as previously described.

The geometrically configured slide body 15, preferably of nylon, is generally of a tubular shape including the bore 104 having multiple internal radii. The distally located large radius portion of the bore 104 accommodates one end of the connector fitting 14, such connector fitting 14 having a bore 14a for communication between the lumen 106 of the hub 13 and the longer small radius portion of the bore 104. Annular grooves 108 and 110 are located along and about the exterior of the slide body 15 for accommodation of O-rings 112 and 114, respectively, which are instrumental in providing a seal and for providing for frictional engagement between the slide tube 16 and the slide body 15, as well as for providing a seal along and about longitudinally opposed elongated slots 116 and 118 located along and about the wall of the slide body 15. A slide button 120 of annular configuration is located around and about the distal end of the slide body 15 for actuation of the slide body 15 longitudinally within the surrounding slide tube 16. The slide body 15 is oriented for sliding movement of variable but defined length limits within the bore 94 of the slide tube 16 according to the length of the elongated slots 116 and 118 by the accommodational engagement of the guide pin 92 through the holes 96 and 97 of the slide tube 16 and the elongated slots 116 and 118 of the slide body 15. The elongated slots 116 and 118 are of sufficient size to allow sliding engagement along the interceding portion of the guide pin 92. The arrangement and alignment of the fixed position guide pin 92 with the elongated slots 116 and 118 provides fixed orientation about the longitudinal axis to prevent rotation of the slide body 15 within the slide tube 16, while still allowing to or fro positioning of the slide body 15 with respect to the slide tube 16 along the longitudinal axis, thus maintaining torqueability therealong.

The high pressure tube 64, in addition to the previously described distal portion having closely associated components including the cutter 62, the high pressure loop emanator 66, and the saddle mount 68, also includes an integral spring section 122 located between the distal and proximal portions of the high pressure tube 64. The proximal end of the high pressure tube 64 extends through the manifold 18 to connectingly terminate at the connector fitting 21, and the distal end of the high pressure tube 64 affixes to the distal portion of the catheter tube 12 as previously described.

MODE OF OPERATION

Figure 13A:
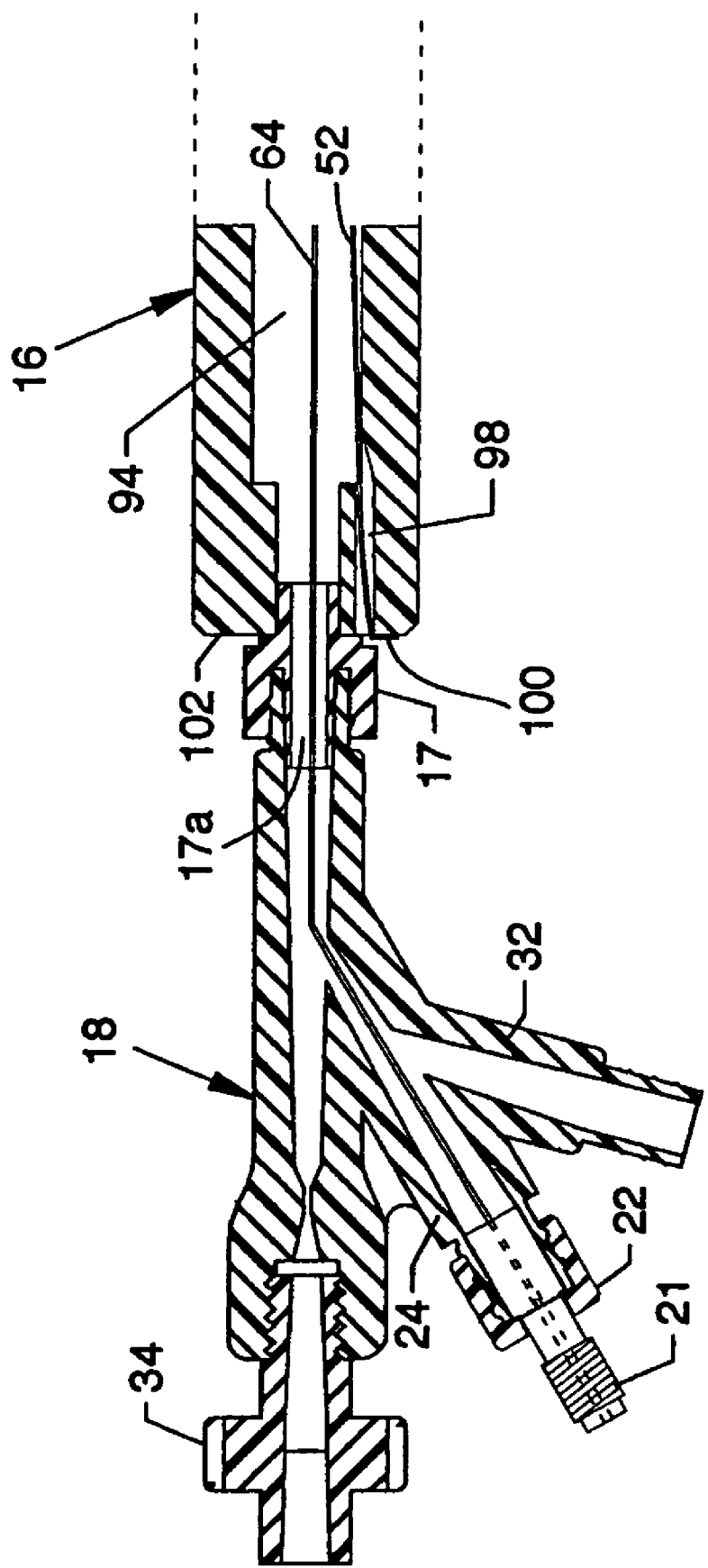
Figure 13B:
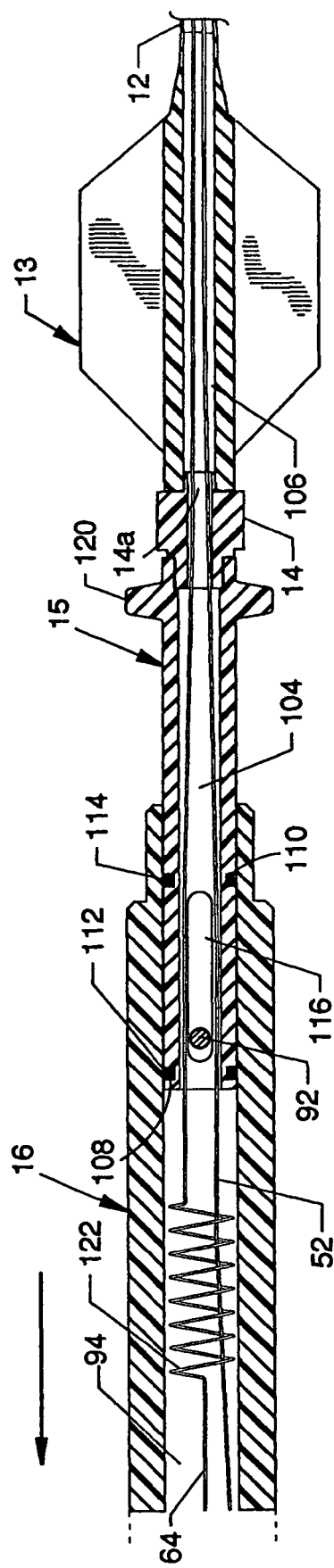

FIG. 12 shows the respective orientation and alignment of FIGS. 13a, 13b and 13c, which are in foreshortened cross section and wherein FIG. 13c is enlarged with respect to FIGS. 13a and 13b. FIGS. 13a, 13b and 13c together are an assembled foreshortened view in cross section of the components of FIGS. 8a and 8b and FIG. 4, including at least the distal portion of the catheter tube 12 and showing components closely associated thereto and therein, such as, but not limited to, the positionable tip 48, the hinge mechanism 46, the notch 50, the uncoated nitinol section 44, the cutter 62, the high pressure tube 64, the high pressure loop emanator 66, the saddle mount 68, the deployment wire 52, the hub 13, the connector fitting 14, the slide body 15, the slide tube 16, the connector fitting 17, and the manifold 18. FIGS. 13a, 13b and 13c show the mechanical functions in the deployed and actuated mode where the positionable tip 48 is actuated about the hinge mechanism 46, as described herein.

Figure 14:
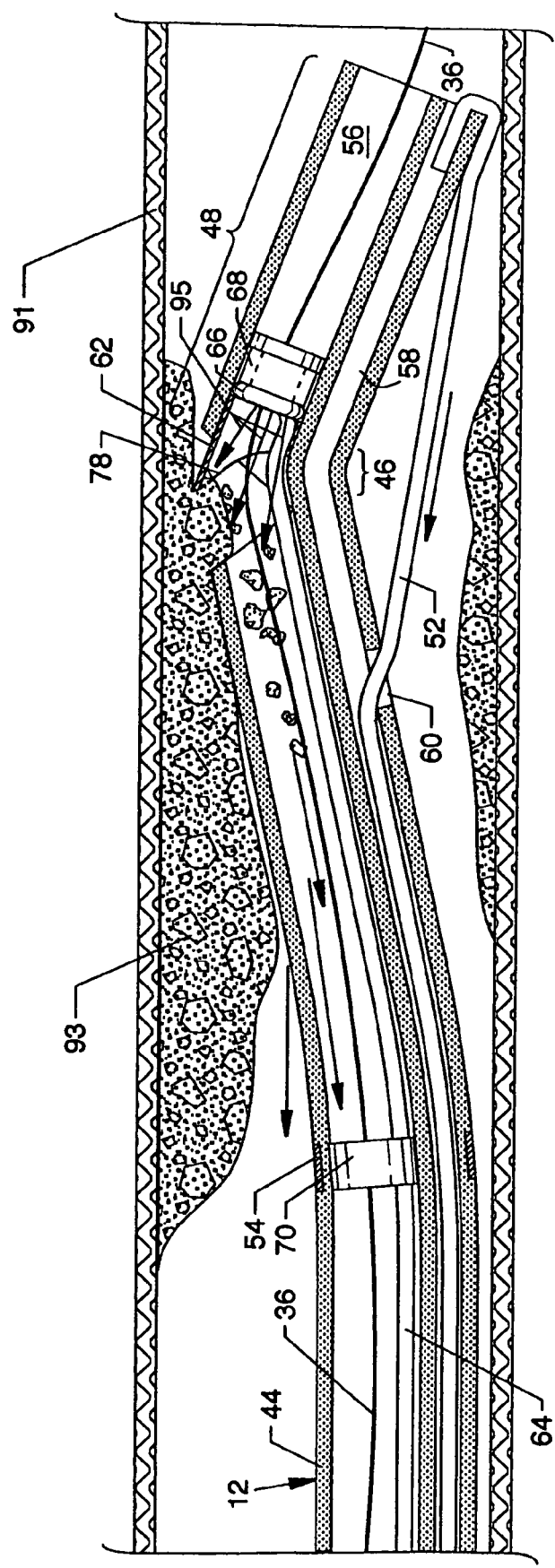
FIG. 14 is a partial cross section view showing a blood vessel accommodating the deployed distal end of the catheter tube of the atherectomy system having a variably exposed cutter.

FIG. 14 is a partial cross section view showing a blood vessel 91 accommodating the deployed distal end of the catheter tube 12 of the atherectomy system having a variably exposed cutter 10, the present invention, and shows and describes interaction of the instant invention with the blood vessel 91 and atheromatous material and/or thrombotic material 93 within the blood vessel 91. Initially, the catheter tube 12 is maneuvered over, about and along a guidewire within the blood vessel 91, such as guidewire 36, by methods known to the art, and is configured and operated according to the method disclosed herein. As such, the unactuated straight profile positionable tip 48, as shown in FIG. 4, is urged distally to a suitable location beyond or in close proximity to a buildup of coagulated blood, plaque, grumous, or other built-up material generally referred to as thrombotic or atheromatous material. With reference to the preceding figures, the mode of operation is further described. Angular deployment of the positionable tip 48 is accomplished by grasping and holding the slide button 120 of the slide body 15 in a stationary position and then grasping the slide tube 16 and retarding the slide tube 16 proximally, thereby changing the relationship of the components of the deployment wire 52 and the high pressure tube 64 with catheter tube 12. The high pressure tube 64 is allowably lengthened by the flexibility of the spring section 122 but the actual finite length of the deployment wire 52 remains unchanged, thereby being instrumental in causing the positionable tip 48 to angularly reposition about the hinge mechanism 46. Such proximal urging of the slide tube 16 also causes free unrestricted passage of the orifice 60 over a small portion of the deployment wire 52. Such proximally directed movement of the slide tube 16 and, thus, the deployment wire 52, interactingly causes pivoting of the positionable tip 48 about the hinge mechanism 46, thereby forming an angular relationship between the positionable tip 48 and the immediate portion of the uncoated nitinol section 44 juxtaposing the proximal portion of the notch 50. During such positioning, the high pressure tube 64 is also temporarily deformed about the hinge mechanism 46. The spring section 122 accommodates the sliding relationship of the slide tube 16 and distally located components or portions of components located distal to the slide tube 16 with respect to the slide body 15 as the slide tube 16 is positioned longitudinally about the slide body 15 for angular positioning of the positionable tip 48 in either direction about the hinge mechanism 46. Proximal movement of the slide tube 16 with respect to the slide body 15 is accommodated by lengthening of the spring section 122 and, conversely, distal movement of the slide tube 16 with respect to the slide body 15 is accommodated by shortening of the spring section 122. Conversely, with respect to the operation of the slide tube 16 and the slide body 15, the slide tube 16 could be held stationary and the slide tube 15 slidingly operated with respect to the slide tube 16, whereby the catheter tube 12 is operated over, about and along the deployment wire 52. As now or as previously described, the high pressure tube 64 springingly accommodates and does not deter or hinder deployment or retraction of the positionable tip 48 about the hinge mechanism 46. In this illustration, the deployed mode configuration relates to an angulated positionable tip 48, such as shown in FIG. 13c, where the relationship of the slide tube 16 to the catheter tube 12 and connected slide body 15 is such that the slide tube 16 engages a minimum portion of the slide body 15, as shown.

The combined combination of the cutter 62, the high pressure loop emanator 66, and the saddle mount 68 is angulated along with the positionable tip 48 to also form an angular relationship with the immediate portion of the uncoated nitinol section 44 juxtaposing the proximal portion of the notch 50. Such positioning widens the breadth and angular displacement of the notch 50 and also reveals the cutting edge 78 of the cutter 62 and extends the cutting edge 78 beyond the profile of the now widened notch 50. When the positionable tip 48 is suitably deployed and angulated, the particular angulation of the positionable tip 48 is maintained by fixation of the position of the deployment wire 52 relative to both the catheter tube 12 and the uncoated nitinol section 44 of the catheter tube 12 by the frictional engagement provided by the O-rings 112 and 114, and then unitarily moved as such an arrangement, preferably in the proximal direction as shown, to skive away atheromatous material and/or thrombotic material 93 as the unitary combination of the catheter tube 12, the slide body 15, the slide tube 16, and the manifold 18 is reciprocatingly retracted or advanced. Skiving cuts away and pares slices of atheromatous material and/or thrombotic material 93 from the walls of the blood vessel 91. The cutting edge 78 of the cutter 62 is oriented such that the cutting edge 78 is facing proximally. Such orientation favors repeated urging of the deployed catheter tube 12 in the proximal direction, in which direction skiving of atheromatous material and/or thrombotic material 93 is most effective. The degree of angulation of the positionable tip 48 with respect to the general uncoated nitinol section 44 can be varied by adjusting the positional relationship of the catheter tube 12 with respect to the deployment wire 52 using the slide tube 16 and the slide body 15, thereby variably exposing the cutter 62. Distally directed relative positioning of the catheter tube 12 with respect to the deployment wire 52 increases the angle about the hinge mechanism 46 to increase the exposure of the cutter 62 with respect to the uncoated nitinol section 44 for greater skiving action. Proximally directed positioning of the catheter tube 12 from a fully or partially deployed positionable tip 48 with respect to the deployment wire 52 decreases the angle about the hinge mechanism 46 to decrease the exposure of the cutter 62 with respect to the uncoated nitinol section 44 for decreased skiving action.

The present invention also utilizes high velocity saline jets 95 to abrade, remove and evacuate atheromatous material and/or thrombotic material 93 from the interior of the blood vessel 91, as well as to abrade, remove and evacuate skived atheromatous material and/or thrombotic material 93. Activation of the high velocity saline jets 95 is accomplished by the use of the high pressure fluid pump 20 and high pressure fluid source 19 or, in the alternative, with a standard AngioJet® hypotube arrangement using the standard AngioJet® console and piston pump arrangement. The high pressure saline jets 95 macerate the skived atheromatous material and/or thrombotic material 93 and remove it out of the large lumen 56 of the catheter tube 12 in a method similar to that used in a standard AngioJet® catheter. Upon repositioning of the catheter tube 12 distally with reference to the deployment wire 52, the positionable tip 48 is assisted in returning to a straight configuration attributable to the superelastic properties of nitinol. The repositioning of the positionable tip 48 at the uncoated nitinol section of the catheter tube 12 to a straight profile is made possible by the memory of the flexible braided wire which also functions as the housing for the high pressure tube 64. The large lumen 56 functions as the exhaust/waste lumen within the catheter tube 12 in conjunction with the exhaust regulator 28 and the collection chamber 26.

The aforementioned issues with atherectomy devices include vessel safety, embolization, ineffective cutting, and ease of use. The present invention overcomes these issues in the following ways. With respect to vessel safety, the use of a fixed cutter 62 in the present invention versus a rotating cutter enhances the reliability of the present invention with respect to vessel safety. Furthermore, the present invention design has variables, such as tip angulation, shape of the cutter, and sharpness, to control the amount of trade-off between vessel safety and device efficacy. Furthermore, the fluid mechanics of the high velocity high pressure saline jets 95 as they slow down develop a recovered pressure which can be safely harnessed and directed to provide sidewardly exhausted jets to push pliable vessel surfaces away from the fixed cutter 62.

With respect to embolization, the present invention avoids the tip unloading issue of the SilverHawk® since the present invention continually evacuates debris. However, by controlling the evacuation flow rate to be greater than the infused flow rate, the chance for liberated debris to be embolized is minimized. Furthermore, the AngioJet® system is also compatible with distal embolization guidewire products, which should essentially eliminate the chance of embolization events.

With respect to device efficacy, the present invention is similar to the SilverHawk® in its ability to present a mechanical cutter 62 to the atheromatic diseased tissue. A major benefit to the present invention is the coupling of high velocity fluid mechanics along with the mechanical cutter 62. The ability to rapidly remove the liberated atheromatic material speeds up the entire atherectomy procedure, thus increasing the efficacy. The angulation of the positionable tip 48 improves the ability of the present invention to remove material over the previous atherectomy device in U.S. Pat. No. 5,496,267, as previously described. Finally, a discussion of ease of use of the present invention is merited. The entire atherectomy experience includes device setup, through device delivery and through completion of the debulking. In the case of the present invention, it has a smaller crossing profile than the SilverHawk® (7Fr versus 8Fr in the larger vessel models). Thus, present device delivery is equivalent, if not better than, competitive technology. Furthermore, the continuous evacuation of debris is expected to make the debulking procedure itself easier. Finally, to address the weakness of device setup, the AngioJet® system has been modified to significantly reduce the number of setup steps. This system, called AngioJet® Ultra, includes a preconnected AngioJet® catheter and pumps disposable set, and a semi-automated console to detect the catheter configuration, and prime the system. In sum, the present invention, especially when coupled with the AngioJet® Ultra system, is easier to use than competitive products.

FIGS. 15, 16, 17 and 18 disclose the structure and mode of operation of a substitute cutter 200 which is elongated and which is flexible along and about the longitudinal axis thereof.

Figure 15:
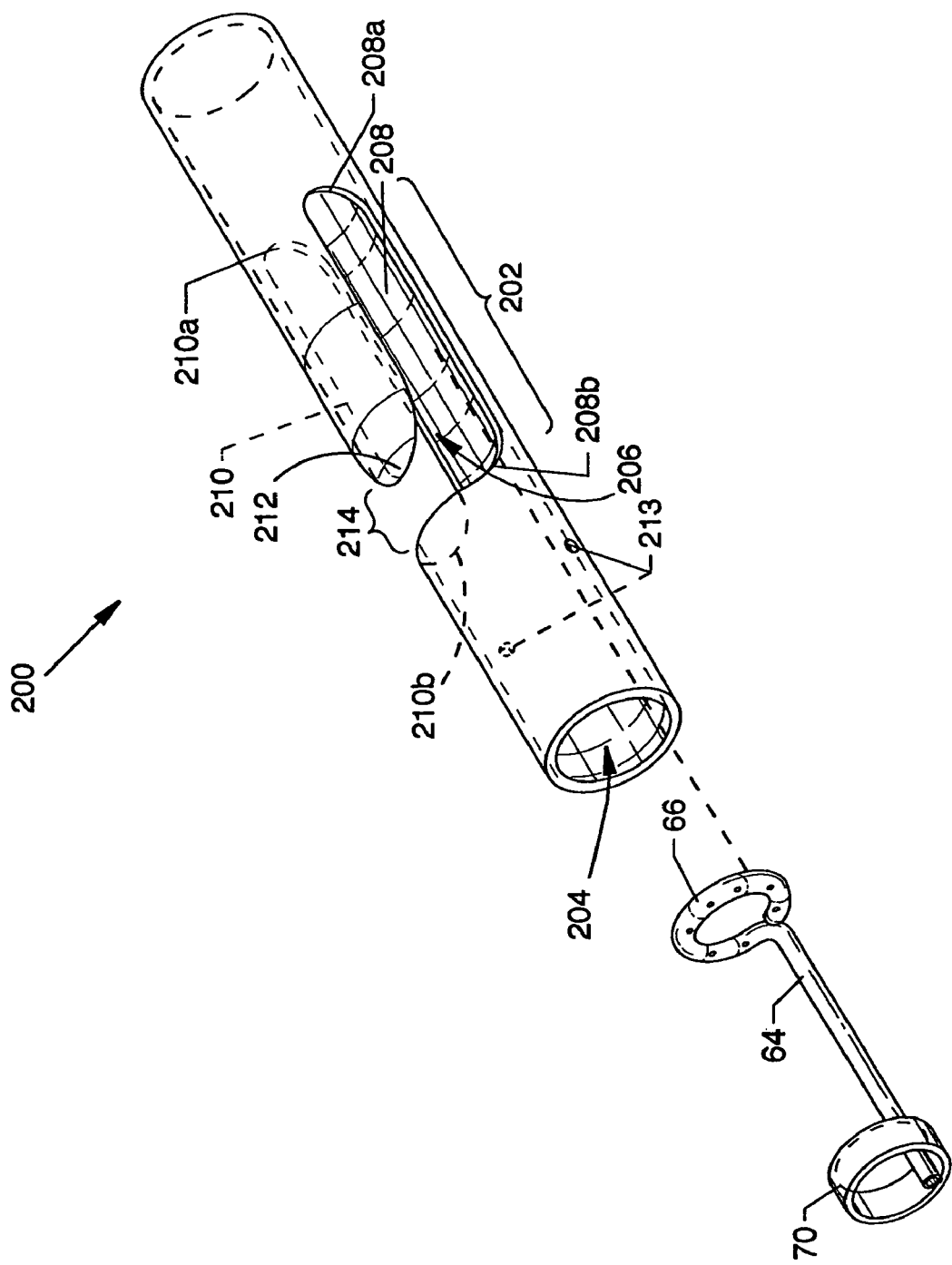
FIG. 15 is an exploded isometric view showing an elongated and flexible cutter, which can be substituted for the cutter shown in FIGS. 2-5, in association with the support ring, the high pressure loop emanator, and portions of the high pressure tube.

FIG. 15 is an exploded isometric view of the elongated and flexible cutter 200, the support ring 70, the high pressure loop emanator 66, and portions of the high pressure tube 64. The high pressure tube 64 is secured, such as by a weldment or other suitable method, to the inner surface of the support ring 70, thereby supporting the high pressure loop emanator 66. The elongated and flexible cutter 200, which is a fixed cutter of nitinol or other suitable material, is generally of tubular form, being geometrically configured to provide for stabilized angulated cutter edge orientation with respect to the longitudinal axis of the elongated and flexible cutter 200, for stabilized orientation of the high pressure loop emanator 66 and associated emanated saline jets 95 with respect to the longitudinal axis of the elongated and flexible cutter 200, and also to provide for flexibility and bending about a narrowed flexible and bendable section 202 of the elongated and flexible cutter 200. A passage 204 extends along the length of the elongated and flexible cutter 200 for accommodation of the support ring 70, the high pressure loop emanator 66, a guidewire, such as guidewire 36, and for evacuation of atheromatous material and/or thrombotic material particulate and saline solution through the proximal portion of the passage 204 of the elongated and flexible cutter 200. A continuously configured cutout 206 along the elongated and flexible cutter 200 includes opposed slots 208 and 210 having distally located closed slot ends 208*a* and 210*a*, respectively, and proximally located open slot ends 208*b* and 210*b*, respectively. The proximally located open slot ends 208*b* and 210*b* form a gap 214 with the end of a cutting edge 212. The flexible and bendable section 202 of the elongated and flexible cutter 200 is the arcuate section extending between the lower edges of the slots 208 and 210. The cutting edge 212 is located as a continuation of and between the upper edges of the slots 208 and 210. Opposed holes 213 extend through the proximal portion of the elongated and flexible cutter 200 to facilitate welding of the elongated and flexible cutter 200 to the support ring 70, as shown in FIG. 17.

Figure 16:
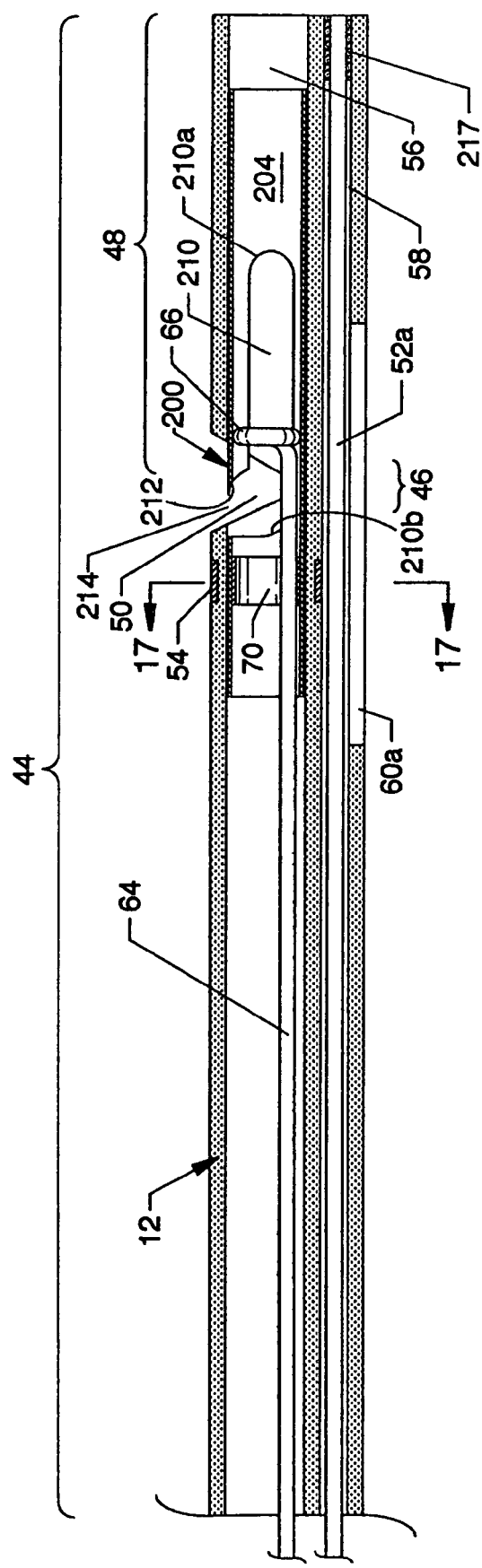
FIG. 16 is an illustration like FIG. 4 but showing the elongated and flexible cutter of FIG. 15 instead of the cutter of FIG. 4.

FIG. 16 is an illustration like FIG. 4 but showing the elongated and flexible cutter 200 instead of the cutter 62. Especially shown is a greater portion of the uncoated nitinol section 44, alternatively comprised of PEBAX®, as well as other components, some of which may be relocated, which align within and thereto. This illustration includes an elongated orifice 60*a*. In this illustration, a redesignated deployment wire 52*a* aligns generally within or in alignment within the small lumen 58, and the distal end of the deployment wire 52*a* secures within the distal portion of the small lumen 58, such as by the use of adhesive 217. The high pressure tube 64 for delivery of high pressure saline extends along the greater length of the large lumen 56 and extends from the connector 21 at the manifold 18, through the manifold 18, through the large lumen 56 and thence into the elongated and flexible cutter 200 and the support ring 70. The greater portion of the elongated and flexible cutter 200, the high pressure loop emanator 66, and the support ring 70, as a unit, are fixed with respect to each other by the weldment of the elongated and flexible cutter 200 to the support ring 70 at holes 213 and by the weldment of the high pressure tube 64 to the support ring 70 shown as weldment 215 in FIG. 17. The elongated aspect of the elongated and flexible cutter 200 lends stability to the operation of the invention in that support is offered by the uncoated nitinol section 44 along the length of the elongated and flexible cutter 200, thus imparting stability to the high pressure loop emanator 66 and the cutting edge 212. The proximal facing cutting edge 212 of the elongated and flexible cutter 200 is shown extending partly into the gap 214 and the notch 50. The elongated and flexible cutter 200, the high pressure loop emanator 66, and the support ring 70, as a unit, are in close alignment within the portion of the large lumen 56 located in and proximal to the positionable tip 48. The portion of the elongated and flexible cutter 200 distal to the cutting edge 212 does not frictionally engage positionable tip 48 so that the bending or flexing of the positionable tip 48 and the flexible and bendable section 202 about the hinge mechanism 46 is unencumbered and not impeded. In this illustration, the nondeployed mode configuration relates to a nonangulated positionable tip 48 where the relationship of the slide tube 16 to the catheter tube 12 and connected slide body 15 is such that the slide tube 16 engages a maximum portion of the slide body 15, as previously shown in FIGS. 11a and 11b.

Figure 17:
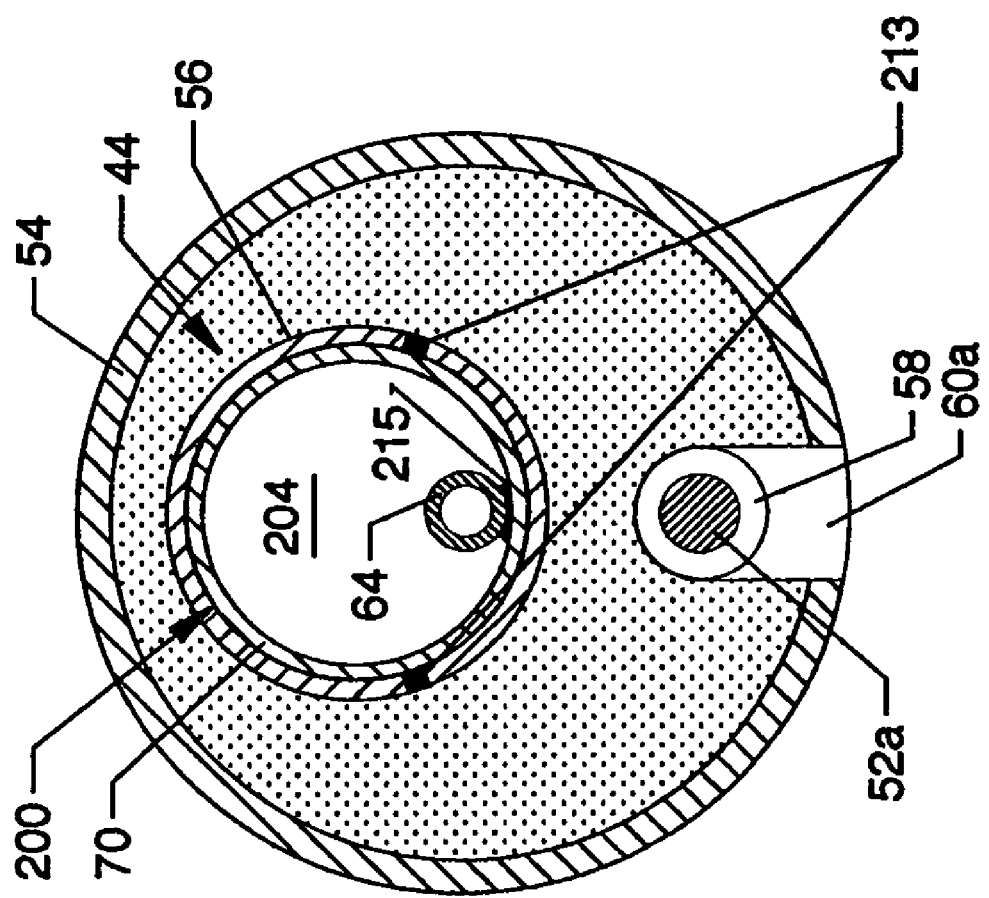
FIG. 17 is a cross section view along line 17-17 of FIG. 16.

FIG. 17 is a cross section view along line 17-17 of FIG. 16.

Mode of Operation of the Invention Using the Substitute Cutter

Figure 18:
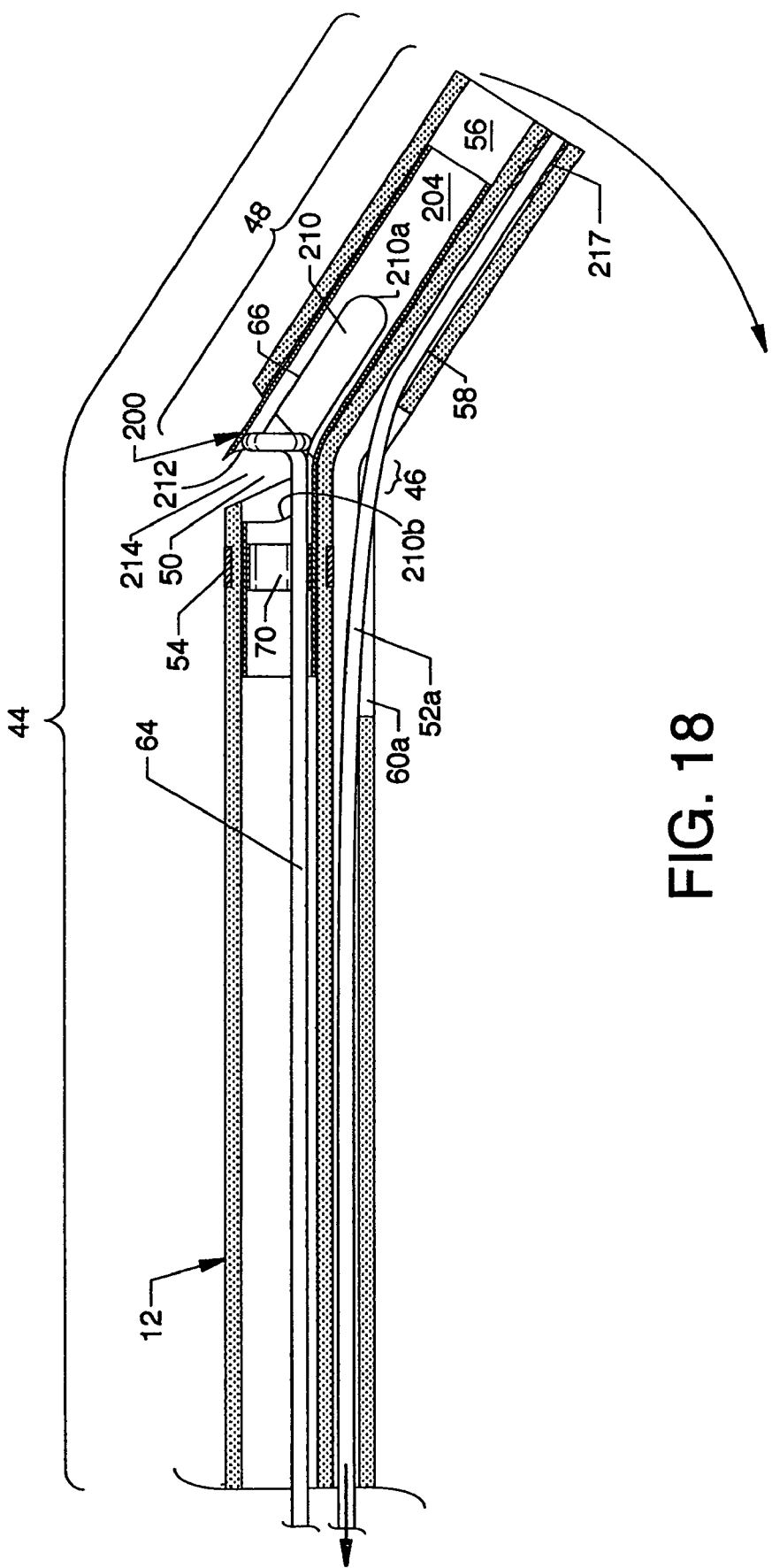
FIG. 18 shows the mechanical functions in the deployed and actuated mode where the positionable tip featuring the elongated and flexible cutter of FIG. 15 is actuated about the hinge mechanism.

FIG. 18 is an illustration like FIG. 13c. FIG. 18 shows the mechanical functions in the deployed and actuated mode where the positionable tip 48 featuring the elongated and flexible cutter 200 is actuated about the hinge mechanism 46. In this illustration, the deployed mode configuration relates to an angulated positionable tip 48, such as shown in FIG. 13c, where the relationship of the slide tube 16 to the catheter tube 12 and connected slide body 15 is such that the slide tube 16 engages a minimum portion of the slide body 15, as shown in FIGS. 13a and 13b.

The elongated and flexible cutter 200 is positionably angulated along with the positionable tip 48 to form an angular relationship with the immediate portion of the uncoated nitinol section 44 juxtaposing the proximal portion of the notch 50. Such positioning widens the breadth and angular displacement of the notch 50 and also reveals the cutting edge 212 of the elongated and flexible cutter 200 and extends the cutting edge 212 beyond the profile of the now widened notch 50. When the positionable tip 48 is suitably deployed and angulated, the particular angulation of the positionable tip 48 is maintained and the invention is operated, as previously described, and then unitarily moved as such an arrangement preferably in a proximal direction to skive away atheromatous material and/or thrombotic material 93 as the unitary combination of the catheter tube 12, the slide body 15, the slide tube 16, and the manifold 18 is reciprocatingly retracted or advanced.

Figure 19:
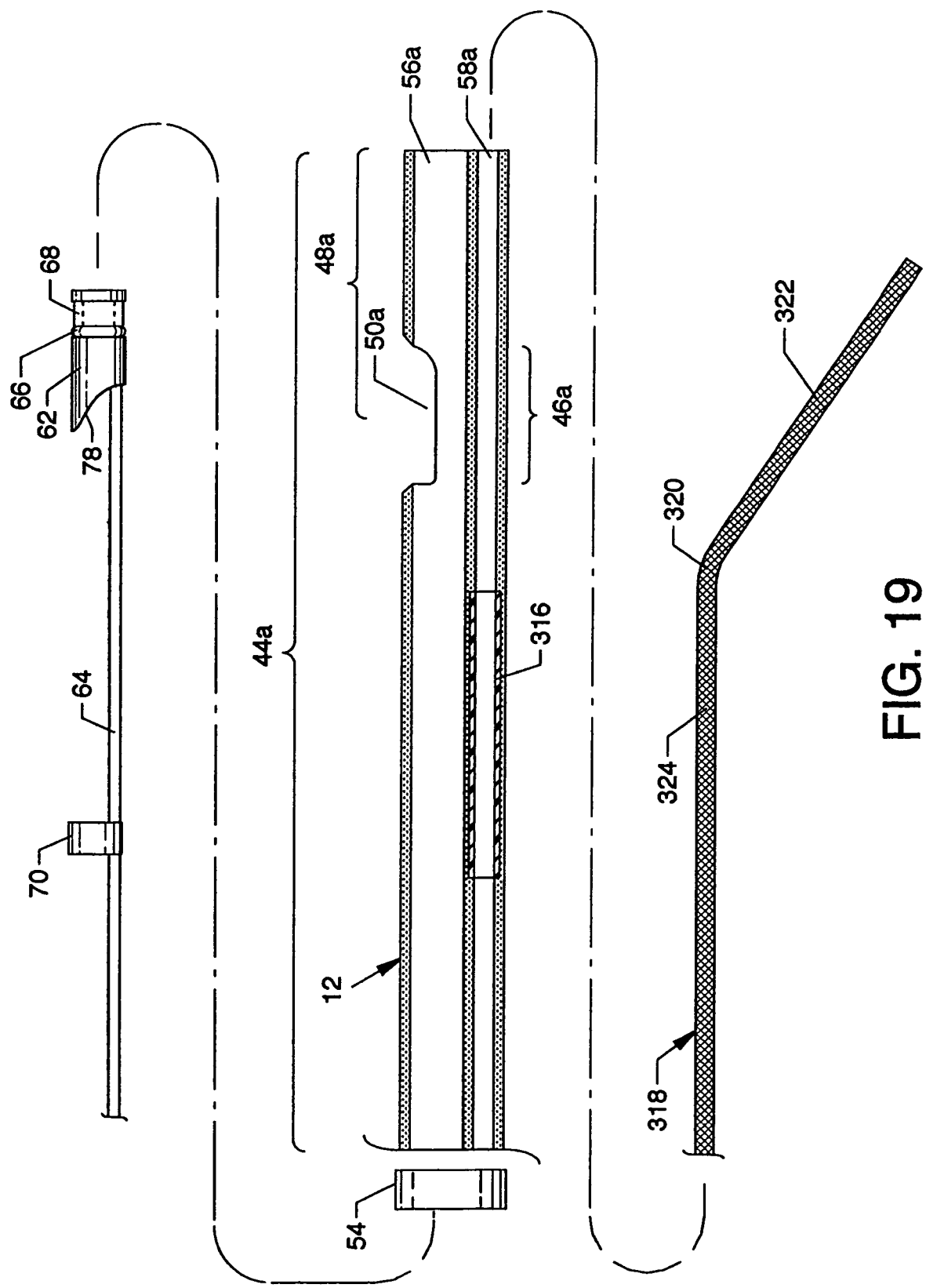
FIG. 19 is a semi-exploded view showing an uncoated nitinol section and contained stiffener tube in cross section and a nitinol actuator, which are components of a first alternative embodiment of the present invention, in association with previously illustrated elements.
Figure 20:
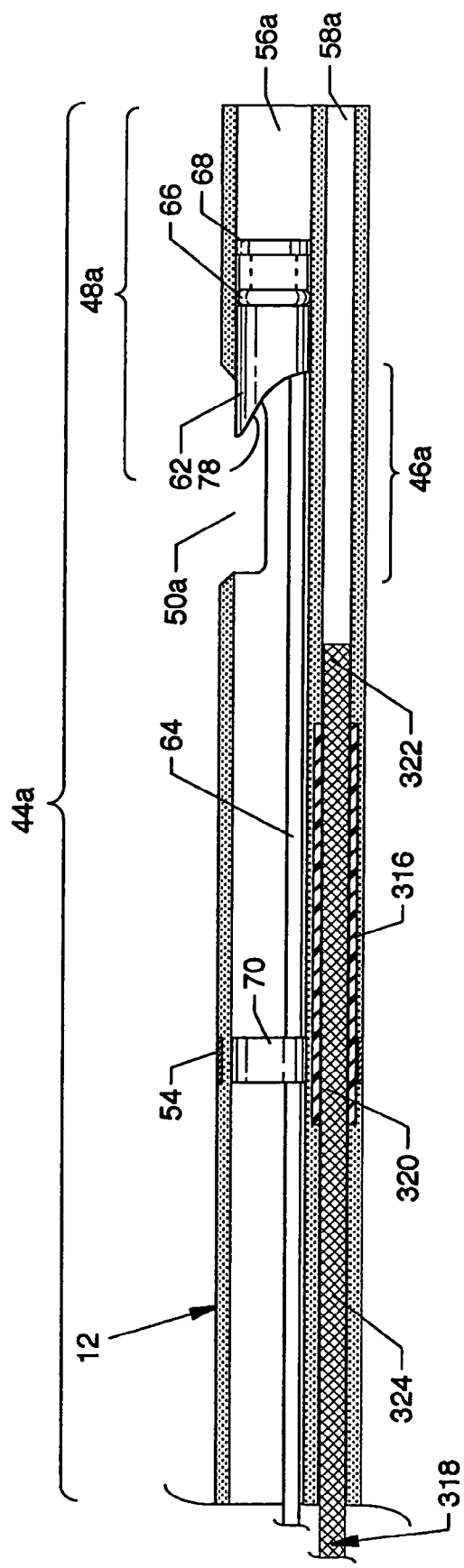
FIG. 20 is an assembled view of the components of FIG. 19 and shows the interaction of the nitinol actuator with the stiffener tube in the uncoated nitinol section when the uncoated nitinol section maintains a straight profile.

FIG. 19 is a semi-exploded view showing an uncoated nitinol section 44a and contained stiffener tube 316 in cross section and a nitinol actuator 318, which are components of a first alternative embodiment of the present invention, in association with previously described components. FIG. 20 is an assembled view of the components shown in FIG. 19. The uncoated nitinol section 44a is generally similar to the previously described uncoated nitinol section 44 including components or features having corresponding reference numerals having "a" suffixed thereto. The uncoated nitinol section 44a is similar in most respects to the previously described uncoated nitinol section 44, but includes structural variations. As with the uncoated nitinol section 44, the uncoated nitinol section 44a includes a large lumen 56a and a small lumen 58a which extend through the catheter tube 12 to connect to the manifold 18 in the same manner previously described. An elongated notch 50a is located in the large lumen 56a in opposition to an elongated hinge mechanism 46a. A stiffener tube 316 is included within the structure of the uncoated nitinol section 44a in a position along and concurrent with and forming part of the small lumen 58a. The stiffener tube 316 is proximal to the elongated hinge mechanism 46a and proximal to the general location of the elongated notch 50a. A nitinol actuator 318 is incorporated in lieu of the deployment wire 52. The nitinol actuator 318 of preset but flexible memory shape and generally in the shape of an angled rod includes an angle section 320 and, adjacent to the angle section 320, a distal section 322 and a proximal section 324. The high pressure tube 64, the high pressure loop emanator 66 at the end of the high pressure tube 64, the cutter 62, and the support ring 70 are utilized with the uncoated nitinol section 44a. It is to be noted that an orifice, such as the orifice 60, is absent from the small lumen 58a of the uncoated nitinol section 44a. In this first alternative embodiment, the nondeployed mode configuration relates to a nonangulated positionable tip 48a, such as shown in FIG. 20, where the relationship of the slide tube 16 to the catheter tube 12 and connected slide body 15 is such that the slide tube 16 engages a minimum portion of the slide body 15, as shown in FIGS. 13a and 13b.

Mode of Operation of the First Alternative Embodiment

Figure 21:
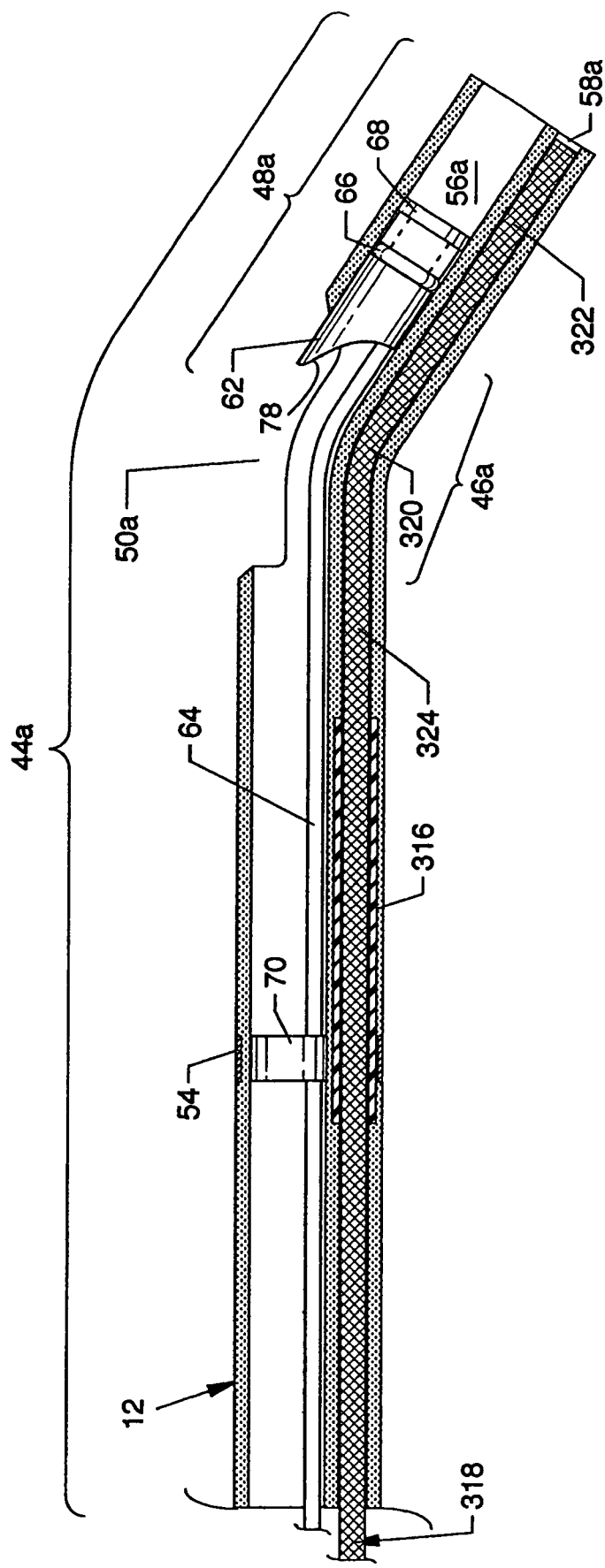
FIG. 21 is a view similar to FIG. 20 showing the interaction of the nitinol actuator with the uncoated nitinol section when the uncoated nitinol section forcibly maintains an angular profile.

FIGS. 20 and 21 illustrate the mode of operation of the first alternative embodiment with respect to the stiffener tube 316 in the uncoated nitinol section 44a and the interaction thereof with the nitinol actuator 318. FIG. 20 shows the interaction of the nitinol actuator 318 with the uncoated nitinol section 44a and the stiffener tube 316, whereby the uncoated nitinol section 44a maintains a straight profile, and FIG. 21 is a view showing the interaction of the nitinol actuator 318 with the uncoated nitinol section 44a and the stiffener tube 316, whereby the uncoated nitinol section 44a forcibly maintains an angular profile.

In FIG. 20, the nitinol actuator 318 is first positioned along and within the small lumen 58a of the uncoated nitinol section 44a by the use of the slide body 15 and the slide tube 16 to cause the uncoated nitinol section 44a to maintain a straight profile to ensure suitable alignment of the angle section 320 within the stiffener tube 316. Contact of the distal section 322, the angle section 320, and the proximal section 324 along the length of the stiffener tube 316 thus causes the nitinol actuator 318 to flexibly straighten about the angle section 320 within the confines of the stiffener tube 316 to resultingly cause the contained portion of the nitinol actuator 318 to assume a straight profile. Correspondingly, the engaged uncoated nitinol section 44a assumes a straight profile as the angle section 320, which is temporarily straightened, does not influence the overall general straight profile shape of the uncoated nitinol section 44a due to the constraining influence and relationship of the nitinol actuator 318 by the stiffener tube 316. Subsequent to ensuring a straight profile of the uncoated nitinol section 44a, the catheter tube 12, including the uncoated nitinol section 44a, the hub 13, the slide body 15, the slide tube 16, the manifold 18, and other suitably associated components, are advanced unitarily to position the positionable tip 48a distally to a suitable location beyond or in close proximity to a buildup of coagulated blood, plaque, grumous, or other built-up material generally referred to as thrombotic or atheromatous material 93.

In FIG. 21, the angle section 320 of the nitinol actuator 318 interacts with the uncoated nitinol section 44a, whereby the uncoated nitinol section 44a forcibly maintains an angular profile of the positionable tip 48 about the hinge mechanism 46a. In this illustration of the first alternative embodiment, the deployed mode configuration relates to an angulated positionable tip 48a, such as shown in FIG. 21, where the relationship of the slide tube 16 to the catheter tube 12 and connected slide body 15 is such that the slide tube 16 engages a maximum portion of the slide body 15, as shown in FIGS. 11a and 11b. The nitinol actuator 318 is positioned distally and along the stationary small lumen 58a of the catheter tube 12, whereby the angle section 320 of the nitinol actuator 318 is out of direct contact and influence of the stiffener tube 316. As a result of the repositioning of the nitinol actuator 318, distally the shape of the nitinol actuator 318 is unrestricted and allowed to return substantially to the same angled configuration as dictated by the positional memory. Correspondingly, the positionable tip 48*a* of the engaged uncoated nitinol section 44*a* is influenced by the unrestricted angle section 320 and assumes an angled relationship about the elongated hinge assembly 46*a* relating to the angle section 320 of the nitinol actuator 318.

The first alternative embodiment of the present invention operates much in the same manner as prescribed for the other embodiments using high velocity saline jets to abrade, remove and evacuate atheromatous material and/or thrombotic material 93 from the interior of a blood vessel 91, as well as to abrade, remove and evacuate skived atheromatous material and/or thrombotic material 93. As in the other embodiments, the cutting edge 78 of the cutter 62 is oriented such that the cutting edge 78 is facing proximally. Such orientation favors urging of the deployed catheter tube 12 in a proximal direction where skiving of atheromatous material and/or thrombotic material 93 is most effective. The degree of angulation of the positionable tip 48*a* with respect to the general uncoated nitinol section 44*a* can be varied by the use of a different nitinol actuator 318 having a different angle at angle section 320. Increasing the angle at angle section 320 of a different nitinol actuator 318 increases the angle about the hinge mechanism 46*a* to increase the exposure of the cutter 62 with respect to the uncoated nitinol section 44*a* for greater skiving action.

Decreasing the angle at the angle section 320 of the different nitinol actuator 318 decreases the angle about the hinge mechanism 46*a* to decrease the exposure of the cutter 62 with respect to the uncoated nitinol section 44*a* for decreased skiving action. Activation of high velocity saline jets is accomplished by the use of the high pressure fluid pump 20 and the high pressure fluid source 19, or in the alternative, with a standard AngioJet® hypotube arrangement using the standard AngioJet® console and piston pump arrangement. The high pressure saline jets 95 macerate the skived atheromatous and/or thrombotic material 93 and remove it out of the large lumen 56*a* of the catheter tube 12 in a method similar to that used in a standard AngioJet® catheter. After removal of the atheromatous material and/or thrombotic material 93, repositioning of the nitinol actuator 318 proximally along the uncoated nitinol section 44*a* forces the angle section 320 of the nitinol actuator 318 into a straight profile incorporating the influence of the stiffener tube 316. The hinge mechanism 46*a* of the uncoated nitinol section 44*a* returns to a straight configuration attributable to the superelastic properties of nitinol, thereby aligning the positionable tip 48*a* to the region of the uncoated nitinol section 44*a* which is immediately proximal to the elongated hinge mechanism 46*a*. The repositioning of the positionable tip 48*a* at the uncoated nitinol section 44*a* of the catheter tube 12 to a straight profile is made possible by the memory of the flexible braided wire. The large lumen 56*a* functions as the housing for the high pressure tube 64 and as the exhaust/waste lumen within the catheter tube 12 in conjunction with use of the exhaust regulator 28 and the collection chamber 26.

Figure 22:
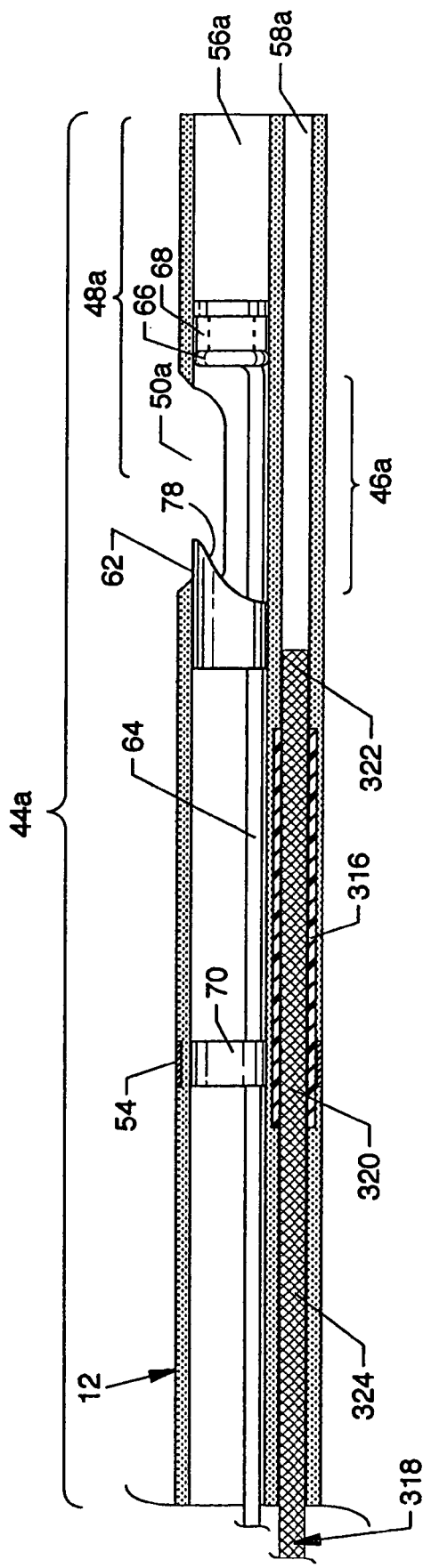
FIG. 22 is a view showing an uncoated nitinol section and contained stiffener tube in cross section and a nitinol actuator incorporated with a cutter which is reversed, thereby forming a second alternative embodiment of the present invention.
Figure 23:
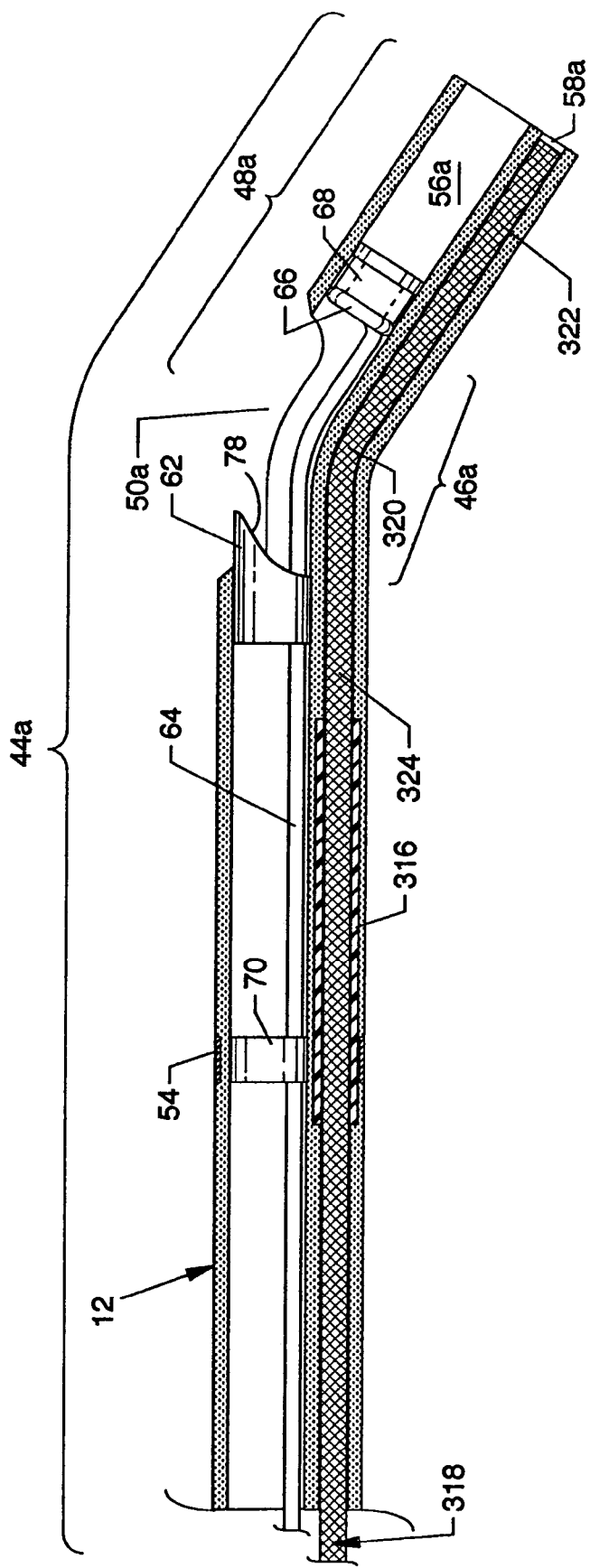
FIG. 23 is a view similar to FIG. 22 showing the interaction of the nitinol actuator with the uncoated nitinol section when the uncoated nitinol section forcibly maintains an angular profile.

FIG. 22 is a view showing the uncoated nitinol section 44*a* and contained stiffener tube 316 in cross section and the nitinol actuator 318 incorporated with a cutter which is reversed, thereby forming a second alternative embodiment of the present invention. FIG. 23 is a view similar to FIG. 22 showing the interaction of the nitinol actuator 318 with the uncoated nitinol section 44*a* when the uncoated nitinol section 44*a* maintains an angular profile. The cutter 62 is spaced from the high pressure loop emanator 66 and reversed with respect to the position shown in the second alternative embodiment and secured to the high pressure tube 64, such as by the use of a weldment or other suitable method. The cutter 62 aligns in the large lumen 56*a* at the proximal portion of the elongated notch 50*a* and is oriented such that the cutting edge 78 faces distally.

Mode of Operation of the Second Alternative Embodiment

FIGS. 22 and 23 illustrate the mode of operation of the second alternative embodiment with respect to the uncoated nitinol section 44*a* and stiffener tube 316 and the interaction thereof with the nitinol actuator 318. FIG. 22 is a view showing the interaction of the nitinol actuator 318 with the uncoated nitinol section 44*a* and the stiffener tube 316, whereby the uncoated nitinol section 44*a* maintains a straight profile, and FIG. 23 is a view showing the interaction of the nitinol actuator 318 with the uncoated nitinol section 44*a* and the stiffener tube 316, whereby the uncoated nitinol section 44*a* forcibly maintains an angular profile.

The second alternative embodiment of the present invention operates much in the same manner as prescribed for the other embodiments and also uses high velocity saline jets to abrade, remove and evacuate atheromatous material and/or thrombotic material 93 from the interior of a blood vessel 91, as well as to abrade, remove and evacuate skived atheromatous material and/or thrombotic material 93. As an alternative to the other embodiments, the cutting edge 78 of the cutter 62 is oriented such that the cutting edge 78 is facing distally. Such orientation favors urging of the deployed catheter tube 12 in a distal direction where skiving of atheromatous material and/or thrombotic material 93 is most effective.

Figure 24:
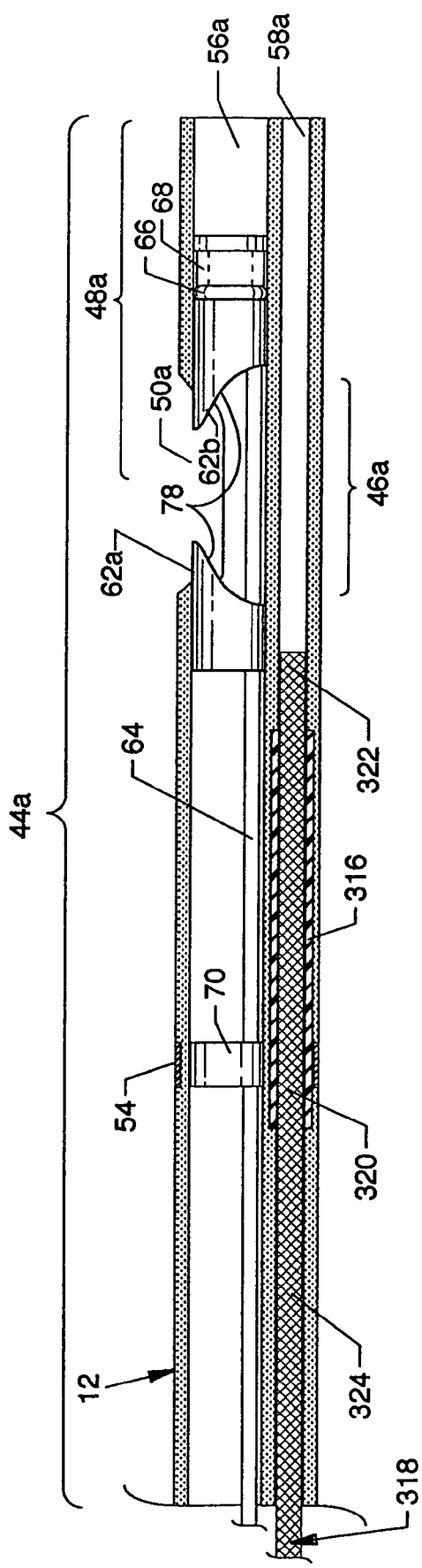
FIG. 24 is a view showing an uncoated nitinol section and contained stiffener tube in cross section and a nitinol actuator incorporated with reversed cutters, thereby forming a third alternative embodiment of the present invention; and, FIG. 25 is a view similar to FIG. 24 showing the interaction of the nitinol actuator with the uncoated nitinol section when the uncoated nitinol section forcibly maintains an angular profile.
Figure 25:
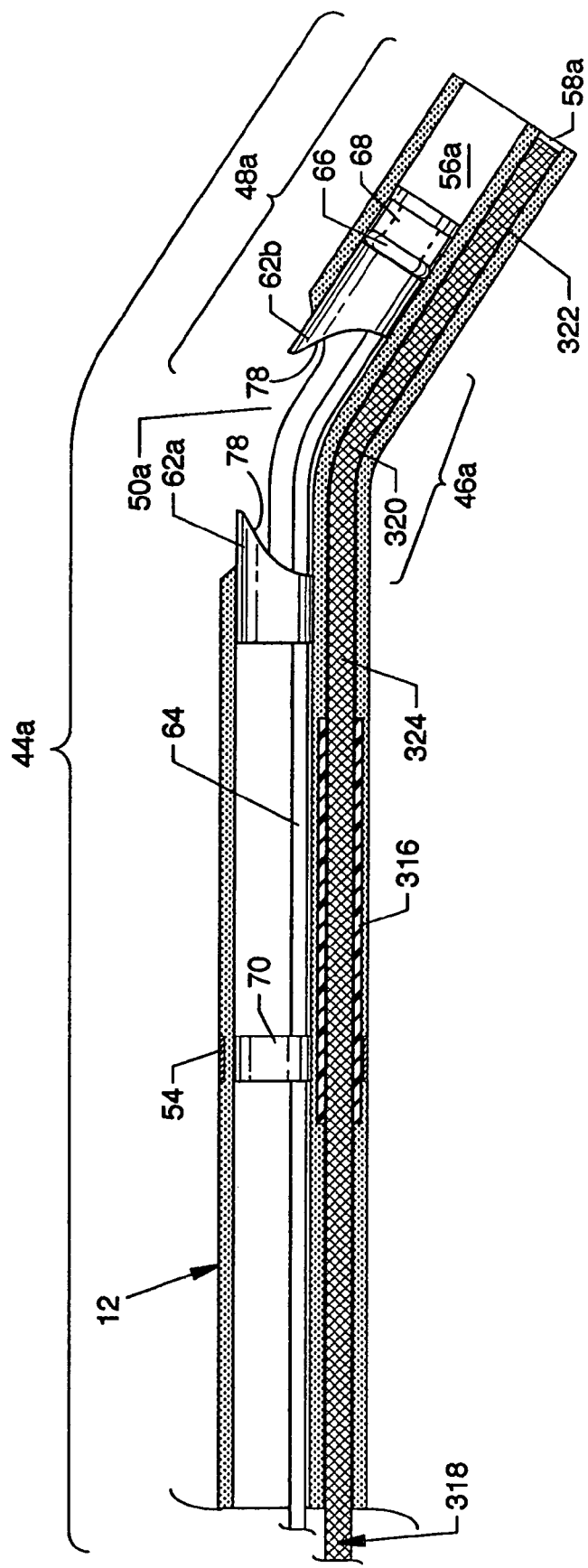

FIG. 24 is a view showing the uncoated nitinol section 44*a* and contained stiffener tube 316 in cross section and the nitinol actuator 318 incorporated into use with appropriately attached opposed cutters 62*a* and 62*b*, thereby forming a third alternative embodiment of the present invention. FIG. 25 is a view similar to FIG. 24 showing the interaction of the nitinol actuator 318 with the uncoated nitinol section 44*a* when the uncoated nitinol section 44*a* maintains an angular profile. The cutter 62*a* is spaced from the high pressure loop emanator 66 and secured to the high pressure tube 64, such as by the use of a weldment or other suitable method, and cutter 62*b* is appropriately secured to the high pressure loop emanator 66. The cutter 62*a* aligns in the large lumen 56*a* at the proximal portion of the elongated notch 50*a* and is oriented such that the cutting edge 78 faces distally, and the cutter 62*b* aligns in the large lumen 56*a* at the distal portion of the elongated notch 50*a* and is oriented such that the cutting edge 78 faces proximally.

Mode of Operation of the Third Alternative Embodiment

FIGS. 24 and 25 illustrate the mode of operation of the third alternative embodiment with respect to the uncoated nitinol section 44*a* and stiffener tube 316 and the interaction thereof with the nitinol actuator 318. FIG. 24 is a view showing the interaction of the nitinol actuator 318 with the uncoated nitinol section 44*a* and the stiffener tube 316, whereby the uncoated nitinol section 44*a* maintains a straight profile, and FIG. 25 is a view showing the interaction of the nitinol actuator 318 with the uncoated nitinol section 44*a* and the stiffener tube 316, whereby the uncoated nitinol section 44*a* forcibly maintains an angular profile.

The third alternative embodiment of the present invention operates much in the same manner as prescribed for the other embodiments and also uses high velocity saline jets to abrade, remove and evacuate atheromatous material and/or thrombotic material 93 from the interior of a blood vessel 91, as well as to abrade, remove and evacuate skived atheromatous material and/or thrombotic material 93. As an alternative to the other embodiments, the cutting edge 78 of the cutter 62a is oriented such that the cutting edge 78 is facing distally, and the cutting edge 78 of the cutter 62b is oriented such that the cutting edge 78 is facing proximally. Such orientation favors urging of the deployed catheter tube 12 in both a distal direction and a proximal direction where skiving of atheromatous material and/or thrombotic material 93 is unilaterally effective in both directions.

Various modifications can be made to the present invention without departing from the apparent scope thereof.

PARTS LIST 10 atherectomy system having a variably exposed cutter
12 catheter tube
13 hub
14 connector fitting
14a bore
15 slide body
16 slide tube
17 connector fitting
17a bore
18 manifold
19 high pressure fluid source
20 high pressure fluid pump
21 connector fitting
22 connector fitting
24 high pressure branch
26 collection chamber
28 exhaust regulator
30 connector fitting
32 exhaust branch
34 hemostatic nut
36 guidewire
42 plastic coated nitinol section
44 uncoated nitinol section
44a uncoated nitinol section
46 hinge mechanism
46a elongated hinge mechanism
48 positionable tip
48a positionable tip
50 notch
50a elongated notch
52 deployment wire
52a deployment wire
54 radiopaque ring
56 large lumen
56a large lumen
58 small lumen
58a small lumen
60 orifice
60a elongated orifice
62 cutter
62a cutter
62b cutter
64 high pressure tube
66 high pressure loop emanator
68 saddle mount
70 support ring
72a-n jet orifices
74 lumen
76 passage
78 cutting edge
80 annular surface
82 passage
84 minor radius portion
86 major radius portion
88 passage
90 annular surface
91 blood vessel
92 guide pin
93 atheromatous material and/or thrombotic material
94 bore
95 saline jet
96 hole
97 hole
98 anchoring passage
100 proximal end
102 proximal annular surface
104 bore
106 lumen
108 annular groove
110 annular groove
112 O-ring
114 O-ring
116 elongated slot
118 elongated slot
120 slide button
122 spring section
200 elongated and flexible cutter
202 flexible and bendable section
204 passage
206 cutout
208 slot
208a closed slot end
208b open slot end
210 slot
210a closed slot end
210b open slot end
212 cutting edge
213 hole
214 gap
215 weldment
217 adhesive
316 stiffener tube
318 nitinol actuator
320 angle section
322 distal section
324 proximal section It is claimed:

1. An atherectomy system comprising:
   a. a catheter tube, the catheter tube having a proximal end and a distal end, a first lumen and a second lumen, the second lumen smaller in diameter than the first lumen, the catheter tube comprising:
      (1) a hinge mechanism in the catheter tube that comprises a notch that interrupts an outer surface of the catheter tube and extends into the first lumen of the catheter tube; and
      (2) a positionable tip extending distally from the hinge mechanism, wherein rotation of the hinge mechanism pivots the positionable tip relative to a portion of the catheter tube located proximal the hinge mechanism;
   b. a high pressure tube within the first lumen, the high pressure tube having a proximal end and a distal end, the distal end extending past the hinge mechanism and into the positionable tip, the high pressure tube terminating in a distally located fluid jet emanator, the fluid jet emanator having proximally facing jet orifices from which a high pressure fluid is emitted; and c. a fixed cutter located at a fixed position within the first lumen and secured to the fluid jet emanator, the cutter comprising a cutting surface that is always exposed within the notch of the hinge mechanism;

wherein the atherectomy system does not use a separate suction source.

2. The atherectomy system of claim 1, further comprising a high pressure fluid source and high pressure pump connected to the proximal end of the high pressure tube.

3. The atherectomy system of claim 1, further comprising a collection chamber and exhaust regulator connected to the first lumen.

4. The atherectomy system of claim 1, further comprising an orifice located in the catheter tube proximal to the notch and extending into the second lumen.

5. The atherectomy system of claim 4, wherein a deployment wire passes from the proximal end of the second lumen through the orifice located proximal the notch and extends externally to fixedly engage the positionable tip.

6. The atherectomy system of claim 5, wherein partially retracting the deployment wire proximally causes the positionable tip to angularly reposition about the hinge mechanism.

7. The atherectomy system of claim 6, wherein the high pressure tube includes a spring portion for accommodating changes in length of the catheter tube attributable to angular movement at the hinge mechanism.

8. The atherectomy system of claim 5, wherein the deployment wire is controllable by attachment to and manipulation of a slide tube.

9. The atherectomy system of claim 8, wherein the cutting surface of the cutter is increasingly and controllably deployed from the notch, with the cutting surface extending beyond the profile of the catheter tube when the deployment wire is pulled proximally.

10. An atherectomy system comprising:
a. a catheter tube, the catheter tube having a proximal end and a distal end, a first lumen and a second lumen, the second lumen smaller in diameter than the first lumen and located parallel to the first lumen, the catheter tube comprising:
(1) a flexible and bendable section comprising a gap interrupting an outer surface of the catheter tube and extending into the first lumen of the catheter tube;
(2) a positionable tip extending distally from the flexible and bendable section, wherein rotation of the catheter tube at the flexible and bendable section pivots the positionable tip relative to a portion of the catheter tube located proximal the flexible and bendable section;
b. a high pressure tube within the first lumen, and having a proximal end and a distal end, the distal end extending past the hinge mechanism and into the positionable tip, the high pressure tube terminating in a distally located fluid jet emanator having proximally facing jet orifices from which a high pressure fluid is emitted; and
c. a fixed cutter located at a fixed position within the first lumen and secured to the fluid jet emanator, the cutter comprising a cutting surface that is always exposed within the gap interrupting the first lumen of the catheter tube;

wherein the atherectomy system does not use a separate suction source.

11. The atherectomy system of claim 10, further comprising a high pressure fluid source and high pressure pump connected to the proximal end of the high pressure tube.

12. The atherectomy system of claim 10, further comprising a collection chamber and exhaust regulator connected to the first lumen.

13. The atherectomy system of claim 10, further comprising an orifice located in the catheter tube proximal to the gap and extending into the second lumen.

14. The atherectomy system of claim 13, wherein a deployment wire passes from the proximal end of the second lumen through the orifice located proximal the gap and extends externally to fixedly engage the positionable tip.

15. The atherectomy system of claim 14, wherein partially retracting the deployment wire proximally causes the positionable tip to angularly reposition about the flexible and bendable section.

16. The atherectomy system of claim 15, wherein the deployment wire is controllable by attachment to and manipulation of a slide tube.

17. The atherectomy system of claim 16, wherein the cutting surface of the cutter is increasingly and controllably deployed from the gap, with the cutting surface extending beyond the profile of the catheter tube when the deployment wire is pulled proximally.

18. The atherectomy system of claim 1, wherein the cutting surface comprises a proximally facing cutting surface.

19. The atherectomy system of claim 1, wherein the cutting surface comprises a proximally facing cutting surface, and wherein at least a portion of the cutter is located within the positionable tip.

20. The atherectomy system of claim 1, wherein the cutting surface is located proximal from the jet orifices of the fluid jet emanator.

21. The atherectomy system of claim 1, wherein rotation of the hinge mechanism changes an angular position of the cutting surface relative to the portion of the catheter tube located proximal the hinge mechanism.

22. The atherectomy system of claim 1, wherein the cutting surface comprises a distally facing cutting surface.

23. The atherectomy system of claim 1, wherein the cutting surface comprises a distally facing cutting surface, and wherein at least a portion of the cutter is located in the first lumen at a location proximal the notch.

24. The atherectomy system of claim 23, wherein rotation of the hinge mechanism does not change an angular position of the cutting surface relative to the portion of the catheter tube located proximal the hinge mechanism.

25. The atherectomy system of claim 1, wherein the cutter is located on a distal side of the notch and wherein the cutting surface of the cutter comprises a proximally facing cutting surface, and wherein the system further comprises an opposing cutter located on a proximal side of the notch, wherein the opposing cutter comprises a distally facing cutting surface.

26. The atherectomy system of claim 25, wherein the proximally facing cutting surface and the distally facing cutting surface are both located proximal from the jet orifices of the fluid jet emanator.

27. The atherectomy system of claim 25, wherein rotation of the hinge mechanism changes an angular position of the proximally facing cutting surface relative to the distally facing cutting surface.

28. The atherectomy system of claim 1, wherein the first lumen is parallel to the second lumen.

29. The atherectomy system of claim 1, wherein the catheter tube comprises a proximally located plastic coated nitinol section and a distally located uncoated nitinol section, the uncoated nitinol section being free of plastic coating, and the uncoated nitinol section extending distally from the plastic coated nitinol section.

30. The atherectomy system of claim 29, wherein the hinge mechanism is located in the uncoated nitinol section of the catheter tube.

31. The atherectomy system of claim 29, wherein the hinge mechanism and the positionable tip are located in the uncoated nitinol section of the catheter tube.

32. The atherectomy system of claim 1, wherein the fluid jet emanator is closely aligned within the first lumen but free of frictional engagement so as to allow unimpeded flexing of the hinge mechanism.

33. The atherectomy system of claim 1, wherein the system further comprises a saddle mount secured to a distal facing surface of the fluid jet emanator, the saddle mount having a major radius portion and a minor radius portion and a passage therethrough.

34. The atherectomy system of claim 1, the system further comprising:
- a hub connected to the catheter tube and a connector fitting connected to the hub;
- a slide body connected to the connector fitting;
- a slide tube connected to the slide body;
- a connector fitting connected to the slide tube; and
- a manifold connected to the connector fitting.

35. An atherectomy catheter comprising:
a catheter tube comprising a proximal end and a distal end, the catheter tube further comprising:
- a first lumen extending through the catheter tube, wherein the first lumen extends to the distal end of the catheter tube;
- a notch in an outer surface of the catheter tube that exposes a portion of a first lumen in the catheter tube; and
- a positionable tip extending distally from the notch, wherein the first lumen extends into the positionable tip, and wherein the positionable tip is movable between a straight profile position in which the positionable tip is aligned with a portion of the catheter tube located proximal the notch and positions in which the positionable tip is angularly positioned with respect to the portion of the catheter tube located proximal the notch;

a high pressure tube located within the first lumen, the high pressure tube comprising a proximal end and a distal end, the distal end extending through the portion of the first lumen exposed by the notch and into the positionable tip;

a fluid jet emanator operably attached to the distal end of the high pressure tube in the positionable tip, wherein the fluid jet emanator comprises proximally facing jet orifices from which a high pressure fluid is emitted; and a fixed cutter located within the first lumen and secured to the fluid jet emanator, the fixed cutter comprising a cutting surface that is always exposed within the notch; wherein the atherectomy system does not use a separate suction source.

36. The atherectomy catheter of claim 35, wherein rotation of the positionable tip about the portion of the catheter tube containing the notch changes an angular position of the cutting surface relative to the portion of the catheter tube located proximal the notch.

* * * * *